(12) United States Patent
Constantinides et al.

(10) Patent No.: US 8,535,650 B2
(45) Date of Patent: Sep. 17, 2013

(54) STABILIZED REVERSE MICELLE COMPOSITIONS AND USES THEREOF

(75) Inventors: Panayiotis P. Constantinides, Gurnee, IL (US); Likan Liang, Boyds, MD (US); Eun-Hyun Jang, Cambridge, MA (US)

(73) Assignee: Soligenix, Inc., Princeton, NJ (US)

( * ) Notice: Subject to any disclaimer, the term of this patent is extended or adjusted under 35 U.S.C. 154(b) by 1020 days.

(21) Appl. No.: 10/497,775

(22) PCT Filed: Dec. 3, 2002

(86) PCT No.: PCT/US02/38473
§ 371 (c)(1), (2), (4) Date: Nov. 19, 2004

(87) PCT Pub. No.: WO03/047493
PCT Pub. Date: Jun. 12, 2003

(65) Prior Publication Data
US 2005/0079145 A1    Apr. 14, 2005

Related U.S. Application Data

(60) Provisional application No. 60/336,873, filed on Dec. 3, 2001, provisional application No. 60/354,744, filed on Feb. 5, 2002, provisional application No. 60/377,691, filed on May 3, 2002.

(51) Int. Cl.
*A61K 9/107* (2006.01)
*A61K 31/727* (2006.01)

(52) U.S. Cl.
USPC ........ 424/70.1; 424/70.31; 424/449; 424/450

(58) Field of Classification Search
USPC .............................. 424/70.1, 70.31, 449, 450
See application file for complete search history.

(56) References Cited

U.S. PATENT DOCUMENTS 5,160,740 A   11/1992   Hasegawa et al.
5,292,499 A    3/1994   Evans et al.
(Continued)

FOREIGN PATENT DOCUMENTS

EP    0 225 130       6/1987
JP    5194253    *   8/1993
(Continued)

OTHER PUBLICATIONS

Martini et al , Drug deivery systems for cancer drugs, Expert Opin. Ther. Patents, 13(12) 1801-1807, 2003.*
JP 5194253 translated document , Sakurai Hiroshi, pub date: Aug. 3, 1993, Translated by: Linguistic systems.*
(Continued)

*Primary Examiner* — Savitha Rao
(74) *Attorney, Agent, or Firm* — Lewis Kohn & Fitzwilliam LLP; David M. Kohn; Kari Moyer-Henry

(57) ABSTRACT

The invention relates to compositions and methods for drug delivery suitable for promoting the transmucosal absorption of drugs, especially drugs with poor intrinsic bioavailability, such as peptides, proteins, vaccines, and nucleic acids. The delivery system of this invention preferably comprises fatty acid esters and their hydrophilic derivatives that associate with water and other polar solvents to form reverse micelles that are physically stabilized in the presence of gastrointestinal fluid, water, and other hydrophilic solvents. Such stable reverse micelles are formed by suitable mixtures of polymeric or non-polymeric compounds with amphiphiles. Micelles made using these methods undergo phase transformation more slowly resulting in delayed drug release profiles and sustained absorption. When administered as a pharmaceutical to mucosal surfaces following oral ingestion or intranasal administration, therapeutic molecules principally solubilized in the aqueous phase are protected from digestion by mucosal enzymes and other mucosal degradative processes and are taken up by absorptive cell mechanisms and reach appropriate body compartments. The reverse micelle compositions may comprise mono-, di-glycerides and/or their transesterified products containing C6-C12 fatty acids chains, wherein the transester groups consist of hydrophilic moieties.

18 Claims, 4 Drawing Sheets

(56) References Cited

U.S. PATENT DOCUMENTS

Figure 1:
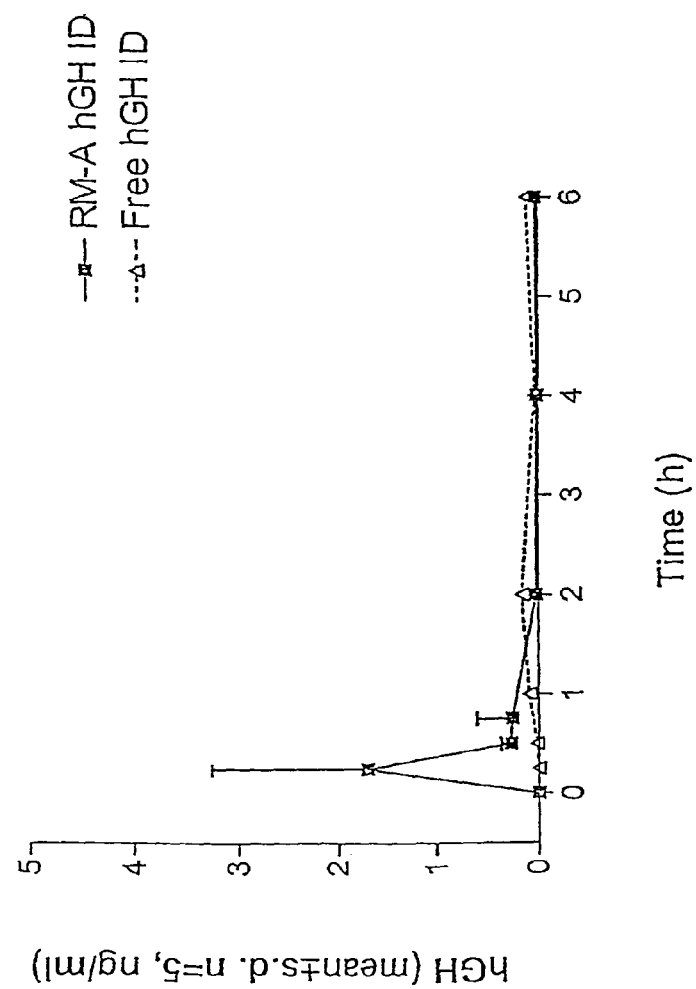

| | | | |
|---|---|---|---|
| 5,451,569 | A | 9/1995 | Wong et al. |
| 5,646,109 | A | 7/1997 | Owen et al. |
| 5,693,516 | A | 12/1997 | Blinkovsky |
| 5,707,648 | A | 1/1998 | Yiv |
| 5,762,904 | A | 6/1998 | Okada et al. |
| 5,942,252 | A | 8/1999 | Tice et al. |
| 5,985,312 | A | 11/1999 | Jacob et al. |
| 6,004,534 | A | 12/1999 | Langer et al. |
| 6,191,105 | B1 | 2/2001 | Ekwuribe et al. |
| 6,245,359 | B1 | 6/2001 | Milstein et al. |
| 6,316,497 | B1 | 11/2001 | Liu et al. |
| 6,417,171 | B1 * | 7/2002 | Maioriello et al. ............ 514/53 |
| 6,485,706 | B1 | 11/2002 | McCoy et al. |
| 6,673,612 | B2 | 1/2004 | Monahan et al. |
| 2003/0059376 | A1 | 3/2003 | Libbey, III et al. |
| 2003/0113366 | A1 | 6/2003 | MacGregor |

FOREIGN PATENT DOCUMENTS

| | | |
|---|---|---|
| WO | 93/02664 | 2/1993 |
| WO | WO 01/93836 | 12/2001 |

OTHER PUBLICATIONS

Chen, et al., Lectin-bearing polymerized liposomes as potential oral vaccine carriers, *Pharmaceutical Research* 13(9):1378-1383(1996).

Constantinides, P.P. Lipid microemulsions for improving drug dissolution and oral absorption: physical and biopharmaceutical aspects, *Pharmaceutical Research* 12(11):1561-1572 (1995).

Mathiowitz, E. et al, Biologically erodable microspheres as potential oral drug delivery systems. *Nature* 386(6623):410-414(1997).

Plosker, G.L., Brogden R.N., Leuprorelin. A review of its pharmacology and therapeutic use in prostatic cancer, endometriosis and other sex hormone-related disorders. *Drugs* 48(6):930-967 (1994).

Regan, Polymerized Liposomes, *Liposomes: from Biophysics to Therapeutics* (Ostro, ed.), pp. 73-109 (1987).

* cited by examiner

STABILIZED REVERSE MICELLE COMPOSITIONS AND USES THEREOF

This application claims the benefit of U.S. provisional application Nos. 60/336,873, filed Dec. 3, 2001; 60/354,744, filed Feb. 5, 2002; and 60/377,691, filed May 3, 2002, each of which is incorporated herein by reference in its entirety.

1. FIELD OF THE INVENTION

The present invention relates to delivery systems for the mucosal and parenteral administration of biologically active molecules, including, but not limited to, therapeutic agents, vaccines, allergens, antigens and diagnostic agents. In particular, the present invention relates to reverse micelle compositions comprising a surfactant, a stabilizer, a hydrophilic phase, and one or more biological active molecules, and methods of administering biologically active molecules to an animal utilizing said compositions. The compositions of the invention promote the absorption of biologically active molecules across mucosal epithelial barriers. The compositions of the invention can be used prophylactically, therapeutically, diagnostically or cosmetically.

2. BACKGROUND OF THE INVENTION

2.1. Drug Delivery

Drug delivery takes a variety of forms, depending on the agent to be delivered and the administration route. The most convenient way to administer drugs into the body is by oral administration. However, many drugs, in particular proteins and peptides, are poorly absorbed and unstable during passage through the gastrointestinal (GI) tract. The administration of these drugs is generally performed through parenteral injection. A large proportion of the macromolecular drugs developed by recombinant DNA methods can be delivered only by injection of the molecules, either subcutaneously or through intravenous administration. Because of the hydrolytic enzymes present and the epithelial barrier of the mucosa, protein and peptide therapeutic molecules are not effective when administered orally or mucosally. The few exceptions to this are several known peptide hormones with molecular weights less than 5,000 daltons, such as calcitonin, nafarelin (luteinizing hormone releasing hormone agonistic analogue) and desmopressin, that penetrate to a limited extent through nasopharyngeal mucosa. These same peptides are therapeutically inactive and not bioavailable when administered orally. Thus, one of the great challenges in the improvement of the therapeutic potential of new macromolecular drugs is the development of systems that will permit oral bioavailability or increased nasal or mucosal bioavailability. A number of systems have been described for such purposes. Further, although many drugs are administered by the oral route and are absorbed either during gastrointestinal transit or in the oral cavity, many hydrophilic drugs are not well absorbed. Many drugs are limited in their development by the parenteral route of administration. Thus, systems that improve the oral or mucosal delivery of a variety of water-soluble compounds are desired.

A variety of microparticulate systems based on entrapment of protein, peptide or nucleic acid therapeutics within the matrix of bioerodable polymer microspheres have been described. Enteric coated formulations have been widely used for many years to protect drugs administered orally, as well as to delay release. For example, U.S. Pat. No. 5,942,252 describes the use of microspheres that are composed of synthetic polymers such as polylactic acid-glycolic acid to form microspheres that can be directed to the intestinal lymphoid tissue for antigen uptake. Entrapping a drug or antigen in a microparticulate system can protect the drug or antigen from acidic and enzymatic degradation, yet still allow the drug or antigen to be administered orally. In this concept, the size of the microspheres less than 10 microns in diameter assists in the sequence of events leading to the uptake of the entire antigen containing particle by cellular endocytosis or related processes. The entrapped drugs or vaccines are taken up by the specialized mucosal tissue and cells, and the vehicles release the entrapped material in a sustained manner. Further, U.S. Pat. No. 5,985,312 describes the use of insulin-containing bioadhesive microcapsules composed of poly-(fumaric acid)-poly-(lactide-co-glycolide) polymers to lower blood glucose levels in experimental animals as a model for the treatment of insulin-dependent diabetes. In some instances, the bioavailability of plasmid DNA and other molecules can be enhanced by microencapsulation in such bioadhesive microspheres. The mechanism of increased activity is thought to be a combination of both paracellular and transcellular transport mechanisms across intestinal epithelia in combination with bioadhesion of the particles to epithelial cell surfaces. (Mathiowitz et al, 1997, *Nature*, 386:410-414).

2.2 Mucosal Delivery

Lipid systems have been widely exploited for development of drug delivery vehicles and systems. Most familiar in the class of lipid vehicles are liposomes. Liposomes are traditionally formed from pure or mixed phospholipids or mixtures with cholesterol or fatty acids. The characteristic feature of liposomes is the formation of an interfacial bilayer membrane that separates an internal water compartment from the external water milieu. Drugs and other active materials can be entrapped within the internal aqueous space. Conventional liposomes have been used successfully to develop commercial pharmaceutical compositions that abrogate the toxicity of certain drugs such as amphotericin, when administered intravenously. A major problem encountered with the development of liposomes as drug delivery vehicles is their poor ability to withstand exposure to stomach acids, bile salts and phospholipases. Nonetheless, one particular approach to improve the GI tract stability of liposomes is by incorporation of certain phospholipids that incorporate polymerizable groups. U.S. Pat. No. 5,160,740 describes polymerization of a polymerizable 2,4-diene phospholipid, cholesterol, and a polymerizable 2,4-diene fatty acid to form a polymerized macromolecular endoplasmic reticulum. Additionally, U.S. Pat. No. 5,762,904 describes the use of polymerized liposomes for the delivery of oral vaccines. Polymerized liposomes are formed from any type of bilayer forming phospholipid or mixture with non-phospholipid structures. The presence of the polymer phospholipid results in a stronger membrane that resists dissolution by detergents and bile salts and is more acid resistant. A number of additional polymerizable phospholipids are described in Regan, in Liposomes: from *Biophysics to Therapeutics* (Ostro, ed., 1987), Marcel Dekker, N.Y. U.S. Pat. No. 6,004,534 describes modifications to the surface of polymerized liposomes in which plant lectins were conjugated. Such lectins recognize receptors on the surface of epithelial cells and promote greater adherence of the liposomes to M cells (Chen et al., 1996, *Pharmaceutical Research* 13:1378-1383). Incorporation of a targeting ligand is believed to increase the efficiency of absorption of drugs encapsulated in those liposomes.

Candidate mucosal delivery systems may additionally incorporate absorption enhancers, such as the salicylates, bile salts and other surfactants. Absorption enhancers may function to increase the permeation of peptide and protein molecules across epithelial barriers because of their interaction with the GI mucosa and concomitant opening of the tight junctions. A wide variety of amphiphilic molecules are known to behave as absorption enhancers. In addition to bile salts and salicylates, medium chain fatty acid salts and esters, and medium chain mono- and di-glycerides are known to have mucosal absorption enhancing activity. Absorption enhancement with these molecules is attributed to the presence of medium chain C6-C12 fatty acyl chains (6-12 carbon atoms in length), particularly those derivatized with C8-C10 fatty acids (8-10 carbon atoms in length). Enhancing molecules may be involved in opening up channels or tight junctions between cells, allowing paracellular transport of co-administered molecules. Furthermore, these molecules may act as inhibitors of intestinal efflux pumps, such as the P-glycoprotein. Other strategies to improve oral delivery include mixing the therapeutic agent with protease inhibitors, such as aprotinin, soybean trypsin inhibitor in an attempt to limit degradation of the administered therapeutic agent. This approach alone, however, has limited commercial utility due to lack of significant absorption enhancement.

Enhanced absorption of protein therapeutic agents across mucosal membranes has also been pursued by using amphiphilic agents that modify the globular nature of protein molecules as described in U.S. Pat. No. 6,245,359. In this case, it is thought that increased penetration across membranes is due to a reversible interaction of the amphiphile with a macromolecule such that the hydrodynamic radius of the molecule is altered enough to penetrate paracellularly.

Each of these strategies has the intent of protecting macromolecules from degradation and promoting the interaction of molecules with absorptive cells in mucosal tissues.

Lipids and surfactants are differentiable from short and long chain hydrocarbons in that they are amphiphilic molecules, having both hydrophilic and hydrophobic moieties. Surfactants are conveniently classified on an empirical scale known as the hydrophile-lipophile balance (HLB) which runs from about 1 to about 45 and from about 1 to about 20 for non-ionic surfactants. HLB values closer to 1 represent surfactants with more lipophilic character, while HLB values that are greater than about 10 represent more hydrophilic surfactants. In contact with water, surfactants form different kinds of aggregates. Phospholipids characteristically form bilayer membranes in water, whereas in water with a low concentration of other polar lipids, micellar structures form. Depending on the concentration of polar lipid in water, micelles are either spherical, typically containing 50-100 lipid molecules, or rod-shaped or disc-shaped macrostructures. In each of these cases, the hydrocarbon tails form the interior of the micelle and polar head groups are contact with water. At higher concentrations of polar lipid in water, reverse-type micelles or reverse micelles form. The conventional micellar phase is also known as the L1 phase. The reverse micellar phase is also known as L2. In the L2 phase, water forms the internal phase and the hydrophobic tails of the lipid form the continuous phase. Reverse micelles containing oil(s), surfactant(s) and an aqueous phase are also characterized as water-in-oil microemulsions (see Constantinides, P.P. Lipid Microemulsions for Improving Drug Dissolution and Oral Absorption: Physical and Biopharmaceutical Aspects, *Pharm. Res.* 12 (11) 1561-1572, 1995 and references therein). In addition, a number of liquid crystalline structures can also co-exist in mixtures of polar lipid and water, analogous to normal and reverse micelles, including hexagonal phases and inverse hexagonal. Traditionally, simple reverse micelles (water/amphiphile) have not been used in mucosal drug delivery systems.

In contrast to reverse micelles, microemulsion systems are ternary or quaternary systems typically formed from an oil phase, a surfactant, and water. For example, U.S. Pat. No. 5,707,648 describes microemulsions that contain an oil phase, an aqueous phase, and a mixture of surfactants. The solubilization of one phase into another in a microemulsion system is affected by a balance of attractive and repulsive forces. As microemulsions are thermodynamically stable, the droplets will not coalesce and precipitate over time. Emulsion droplets are much larger, generally greater than a micron, while microemulsion droplets are in the 10-200 nanometer range. The interface of emulsion droplets can be considered as a monolayer of surfactant. A microemulsion can be characterized by the amount of the dispersed phase solubilized in the continuous phase.

Microemulsions have traditionally been formed using, in addition to the oil phase, one or more surfactants and a cosurfactant, usually short chain alcohols (e.g., ethanol or butanol), glycols (e.g., propylene glycol and polyethylene glycol), medium chain alcohols, amines, or acids.

Citation or identification of any reference in this section, or any section of this application shall not be construed as an admission that such reference is available as prior art to the present invention.

2.3 Luteinizing Hormone-Releasing Hormone Agonists

Luteinizing hormone-releasing hormone (LHRH) agonists and analogs thereof suppress endogenous gonanotropins, causing a hypogonadal condition. Examples of LHRH agonists include, but are not limited to, leuprolide, goserelin, nafarelin and histrelin. Each of these agonists are synthetic analogues of naturally occurring gonadotropin-releasing hormone (GnRH) which has the following amino acid sequence: p-Glu-His-Trp-Ser-Tyr-Gly-Leu-Arg-Pro-Gly-$NH_2$, MW=1182. The modifications to the natural compound result in increased potency and a longer half-life than that of the native peptide. Chronic administration of LHRH agonists exerts constant stimulation of the pituitary gland, leading to long-term inhibition of gonadotropins. In men, testosterone levels are reduced to castrate levels within 14-21 days of therapy, and are reversible upon discontinuation. The primary disease indications for LHRH agonists are prostate cancer, endomettiosis and precocious puberty in children. In addition, the use of LHRH agonists in other disease and disorder indications have been reported (Plosker G. L, Brogden R. N., Leuprorelin. A review of its pharmacology and therapeutic use in prostatic cancer, endometriosis and other sex hormone-related disorders. *Drugs* 1994, 48(6): 930-967). These indications include uterine lelomyomata, fertility disorders, premenopausal breast cancer, endometrial cancer, ovarian cancer, benign prostatic hypertrophy, functional bowel disease, cluster headache, premenstrual syndrome, idiopathic hirsutism or hirsutism second to polycystic ovarian disease, adenomyosis, Meniere's disease, sickle cell anaemia associated priapism and catamental pneumothorax.

No oral dosage forms of LHRH or any of its agonists are available due to the very low oral bioavailability of these molecules (<1%). Thus, there remains a need in the art for any drug delivery approaches that enhance the intestinal absorption and oral bioavailability of these molecules in a patient in need thereof.

Citation or identification of any reference in this section, or any section of this application shall not be construed as an admission that such reference is available as prior art to the present invention.

3. SUMMARY OF THE INVENTION

The present invention provides compositions and methods for the delivery of hydrophilic molecules and other poorly absorbed water-solube molecules to an animal. In particular, the present invention relates to compositions and methods for the delivery of biologically active molecules, including hydrophilic and poorly absorbed water-soluble molecules. In accordance with the present invention, biologically active molecules include, but are not limited to, therapeutic agents, diagnostic agents, antigens, antibodies, peptides, polypeptides, viruses, nucleic acids, growth factors, cytokines, and drugs. The reverse micelle compositions of the present invention promote the absorption of biologically active molecules by mucosal tissues. The reverse micelle compositions of the invention also reduce the dosage of a biologically active molecule necessary to achieve a prophylactic or therapeutic effect in an animal, and thus, reduce the toxicity associated with administering higher dosages of certain biologically active molecules. The reverse micelle compositions of the invention reduce the dosage of a diagnostic agent necessary to diagnose or monitor the state of a disease or disorder in an animal. Further, the reverse micelle compositions of the invention comprising a stabilizer improve the stability of the reverse micelle compositions in the GI tract and result in sustained release of biologically active molecules.

The present invention provides reverse micelle compositions comprising a surfactant (e.g., a P-glycoprotein inhibitor), a hydrophilic phase, and one or more biologically active molecules. In one embodiment, the reverse micelles compositions comprise a P-glycoprotein inhibitor as a surfactant, a hydrophilic phase, a stabilizer and one or more biologically active molecules. In another embodiment, reverse micelle compositions comprise one or more fatty acid esters or hydrophilic derivatives thereof, a hydrophilic phase and one or more biologically active molecules. In accordance with this embodiment, the reverse micelle compositions of the invention comprise less than 15%, less than 10%, less than 5%, or less than 2% by weight of triester. In another embodiment, reverse micelle compositions comprise one or more fatty acid esters or hydrophilic derivatives thereof, a stabilizer, a hydrophilic phase, and one or more biologically active molecules. Preferably, the reverse micelle compositions comprise less than about 15%, less than 10%, less than 5%, or less than 2% by weight of triester and the fatty acids in the fatty acid esters of the reverse micelle compositions have a length of about 6 to about 12 carbon atoms.

In another embodiment, reverse micelle compositions comprise monoglycerides, diglycerides, or hydrophilic derivatives thereof, a hydrophilic phase, a stabilizer and one or more biological active molecules. In another embodiment, reverse micelle compositions comprise monoglycerides or diglycerides or a mixture thereof, a stabilizer, a hydrophilic phase, and one or more biologically active molecules, wherein the acyl groups of the monoglycerides or diglycerides are enriched in fatty acids having 6-12 carbon atoms. In accordance with this embodiment, the monoglycerides or diglycerides may be partially derivatized with a hydrophilic moiety to provide polarity to increase water solubility. Preferably, the reverse micelle compositions comprise less than 15%, less than 10%, less than 5%, or less than 2% by weight of triglycerides.

Optionally, the reverse micelle compositions of the invention are encapsulated for oral delivery in, e.g., starch or gelatin capsules. Further, the reverse micelle compositions of the invention may optionally comprise an adjuvant when the biologically active molecule being administered to an animal is an antigen. The reverse micelle compositions of the present invention have prophylactic and therapeutic utility. The reverse micelle compositions of the present invention also have utility in diagnosing and/or monitoring the state of a variety of diseases and disorders in an animal.

The present invention provides reverse micelle compositions comprising a surfactant (e.g., a P-glycoprotein inhibitor), a stabilizer, a hydrophilic phase, and one or more biologically active molecules, wherein at least one of the biologically active molecules is a protein, polypeptide or peptide. In one embodiment, the surfactant is a P-glycoprotein inhibitor. The present invention also provides reverse micelle compositions comprise one or more fatty acid esters or hydrophilic derivatives thereof, a stabilizer, a hydrophilic phase, and one or more biologically active molecules, wherein at least one of the biologically active molecules is a protein, polypeptide or peptide. In accordance with this embodiment, the reverse micelle compositions comprise less than 15%, less than 10%, less than 5%, or less than 2% by weight of triester. Preferably, the peptides incorporated in the reverse micelle compositions of the invention have a molecular weight ranging from 500 to 10,000 daltons, more preferably from 500 to 5,000 daltons. In particular, hormones (e.g., luteinizing hormone-releasing hormone (LHRH), parathyroid hormone (PTH), calcitonin, insulin, and growth hormone) or agonists thereof (e.g., LHRH agonists) may be incorporated into the reverse micelles of the invention. In a preferred embodiment, reverse micelle compositions comprise one or more fatty acid esters or hydrophilic derivatives thereof, a stabilizer, a hydrophilic phase, and one or more LHRH agonists. Examples of LHRH agonists include, but are not limited to, leuprolide, goserelin, nafarelin and histrelin. Preferably, the LHRH agonist is leuprolide.

In one embodiment, reverse micelle compositions comprise one or more fatty acid esters or hydrophilic derivatives thereof, a stabilizer, a hydrophilic phase, and growth hormone, preferably human growth hormone. In another embodiment, reverse micelle compositions comprise one or more fatty acid esters or hydrophilic derivatives thereof, a stabilizer, a hydrophilic phase, and parathyroid hormone. In another embodiment, reverse micelle compositions comprise one or more fatty acid esters or hydrophilic derivatives thereof, a stabilizer, a hydrophilic phase, and calcitonin. In another embodiment, reverse micelle compositions comprise one or more fatty acid esters or hydrophilic derivatives thereof, a stabilizer, a hydrophilic phase, and a low molecular weight heparin. In another embodiment, reverse micelle compositions comprise one or more fatty acid esters or hydrophilic derivatives thereof, a stabilizer, a hydrophilic phase, and insulin. In accordance with these embodiments, the reverse micelle compositions comprise less than 15%, less than 10%, less than 5%, or less than 2% by weight of triester.

The present invention is based, in part, on Applicants' discovery that the bioavailability of peptide or protein drugs delivered mucosally using reverse micelle compositions comprising medium chain monoglycerides, diglycerides or a mixture thereof (e.g., monoglycerides or diglycerides with 6-12 carbon atom fatty acid side chains) and less than 10% triglycerides are at least equivalent to that of previously known reverse micelles consisting of medium chain monoglycerides, medium chain diglycerides, greater than 20% triglycerides and other surfactants. The present invention is also based, in part, on Applicants' discovery that the simple reverse micelle compositions of the invention provide for high bioavailability of peptides or proteins without the need for complex water-in-oil microemulsions. Further, the present invention is based, in part, on Applicants' surprising discovery that reverse micelle compositions comprising partial monoglycerides, diglycerides or ethoxylated or polyglycolized analogs thereof and polymeric stabilizers incorporate therapeutically effective amounts of therapeutic agents in a biphasic system which is thermodynamically stable and optically clear and transparent (the clarity of the particle being indicative of the presence of an isotropic micelle phase, such as the reverse micelle phase). The incorporation of a polymer within the hydrophobic phase or the interfacial area of the reverse micelle compositions provide stability to the compositions such that leakage of encapsulated biologically active molecules is slower.

The present invention provides methods for the delivery of one or more biologically active molecules to an animal, said methods comprising administering to said animal a reverse micelle composition comprising a surfactant, a hydrophilic phase, and one or more biologically active molecules. More particularly, the present invention provides methods for the delivery of one or more biologically active molecules to an animal, said methods comprising administering to said animal a reverse micelle composition comprising a surfactant, a stabilizer, a hydrophilic phase, and one or more biologically active molecules. In one embodiment, the present invention provides methods for the delivery of one or more biologically active molecules to an animal, said methods comprising administering to said animal a reverse micelle composition comprising one or more fatty acid esters or hydrophilic derivatives thereof, a hydrophilic phase, a stabilizer and one or more biologically active molecules. In accordance with this embodiment, the reverse micelle compositions comprise less than 15%, less than 10%, less than 5%, or less than 2% by weight of triester. Preferably, the fatty acids in the fatty acid esters of the reverse micelle compositions have a length of 6 to 20 carbon atoms, more preferably 6 to 12 carbon atoms, most preferably 8 to 10 carbon atoms. In a specific embodiment, the present invention provides methods for the mucosal delivery of one or more biologically active molecules to an animal, said methods comprising mucosally administering to said animal a reverse micelle composition comprising monoglycerides, diglycerides or hydrophilic derivatives thereof, a stabilizer, a hydrophilic phase, and one or more biological active molecules. In another embodiment, the present invention provides methods for the mucosal delivery of one or more biologically active molecules to an animal, said methods comprising mucosally administering to said animal a reverse micelle composition comprising monoglycerides or diglycerides or a mixture thereof, a stabilizer, a hydrophilic phase, and one or more biologically active molecules, wherein the acyl groups of the monoglycerides or diglycerides are enriched in fatty acids having 6-8, 6-10, 6-12, 8-10, or 8-12 carbon atoms. In accordance with this embodiment, the monoglycerides or diglycerides may be partially-derivatized with a hydrophilic moiety to provide polarity to increase water solubility. Preferably, the reverse micelle compositions administered to an animal comprise less than 15%, less than 10%, less than 5%, or less than 2% by weight of triglycerides.

The present invention provides methods for the prevention, treatment or amelioration of one or more symptoms associated with a disease or disorder, said methods comprising administering to an animal in need thereof an effective amount of a reverse micelle composition comprising a surfactant, a hydrophilic phase, and one or more prophylactic or therapeutic agents useful in the prevention, treatment or amelioration of one or more symptoms associated with said disease or disorder. In particular, the present invention provides methods for the prevention, treatment or amelioration of one or more symptoms associated with a disease or disorder, said methods comprising administering to an animal in need thereof an effective amount of a reverse micelle composition comprising a surfactant, a hydrophilic phase, and one or more prophylactic or therapeutic agents useful in the prevention, treatment or amelioration of one or more symptoms associated with said disease or disorder. In a specific embodiment, the present invention provides methods for the prevention, treatment or amelioration of one or more symptoms associated with a disease or disorder, said methods comprising administering to an animal in need thereof an effective amount of a reverse micelle composition comprising one or more fatty acid esters or hydrophilic derivatives thereof, a hydrophilic phase, a stabilizer and one or more prophylactic or therapeutic agents useful in the prevention, treatment or amelioration of one or more symptoms associated with said disease or disorder. Preferably, the reverse micelle compositions comprise less than 15%, less than 10%, less than 5%, or less than 2% by weight of triester. In a preferred embodiment, the fatty acids of the reverse micelle composition have a length of 6 to 12 carbon atoms.

In another embodiment, the present invention provides methods for the prevention, treatment or amelioration of one or more symptoms associated with a disease or disorder, said methods comprising mucosally administering to an animal in need thereof an effective amount of a reverse micelle composition comprising monoglycerides, diglycerides or hydrophilic derivatives thereof, hydrophilic phase, a stabilizer, and one or more prophylactic or therapeutic agents useful in the prevention, treatment or amelioration of one or more symptoms associated with said disease or disorder. In another embodiment, the present invention provides methods for the prevention, treatment or amelioration of one or more symptoms associated with a disease or disorder, said methods comprising mucosally administering to an animal in need thereof an effective amount of a reverse micelle composition comprising monoglycerides or diglycerides or a mixture thereof, a hydrophilic phase, a stabilizer, and one or more prophylactic or therapeutic agents useful in the prevention, treatment or amelioration of one or more symptoms associated with said disease or disorder, wherein the acyl groups of the monoglycerides or diglycerides are enriched in fatty acids having 6-8, 6-10, 6-12, 8-10, or 8-12 carbon atoms. In accordance with this embodiment, the monoglycerides or diglycerides may be partially derivatized with a hydrophilic moiety to provide polarity to increase water solubility. Preferably, the reverse micelle compositions administered to an animal comprise less than 15%, less than 10%, less than 5%, or less than 2% by weight of triglycerides.

The present invention provides methods for the prevention, treatment or amelioration of one or more symptoms associated with a disease or disorder, said methods comprising administering to said animal a reverse micelle composition comprising a surfactant, a stabilizer, a hydrophilic phase, and one or more biologically active molecules, wherein at least one of the biologically active molecules is a protein, polypeptide or peptide. In a specific embodiment, the present invention provides methods for the prevention, treatment or amelioration of one or more symptoms associated with a disease or disorder, said methods comprising administering to an animal a reverse micelle composition comprising one or more fatty acid esters or hydrophilic derivatives thereof, a stabilizer, a hydrophilic phase, and one or more biologically active molecules, wherein at least one of the biologically active molecules is a protein, polypeptide or peptide. In accordance with this embodiment, the reverse micelle composition administered to said animal comprises less than 15%, less than 10%, less than 5%, or less than 2% by weight of triester. In particular, the present invention provides methods of administering hormones (e.g., luteinizing hormone-releasing hormone (LHRH), parathyroid hormone (PTH), calcitonin, insulin, and growth hormone) and agonists thereof (e.g., LHRH agonists) to animal in need thereof to prevent, treat or ameliorate one or more symptoms associated with a disease or disorder utilizing the reverse micelle compositions of the invention.

In a specific embodiment, the present invention provides methods for the prevention, treatment or amelioration of one or more symptoms associated with prostate cancer, endometriosis, precocious puberty, uterine lelomyotama, fertility disorder, premenopausal breast cancer, endometiral cancer, ovarian cancer, benign prostatic hypertrophy, functional bowel disease, cluster headache, premenstrual syndrome, idiopathic hirsuitism, hirsuitism second to polycycstic ovarian disease, adenomyosis, Mèniére's disease, sickle cell anaemia associated priapism or catamental pneumothorax., said methods comprising administering to an animal in need thereof an effective amount of a reverse micelle composition comprising one or more fatty acid esters or hydrophilic derivatives thereof, a stabilizer, a hydrophilic phase, and one or more LHRH agonists. In another embodiment, the present invention provides methods for the prevention, treatment or amelioration of one or more symptoms associated with hypopituitarism, hypothyroidism, human growth hormone deficiency, Cushing's syndrome, nutritional short stature, intrauterine growth retardation, Russell Silver syndrome or achondroplasia, said methods comprising administering to an animal in need thereof an effective amount of a reverse micelle composition comprising one or more fatty acid esters or hydrophilic derivatives thereof, a stabilizer, a hydrophilic phase, and growth hormone, preferably human growth hormone. In another embodiment, the present invention provides methods for the prevention, treatment or amelioration of one or more symptoms associated with diabetes, said methods comprising administering to an animal in need thereof an effective amount of a reverse micelle composition comprising one or more fatty acid esters or hydrophilic derivatives thereof, a stabilizer, a hydrophilic phase, and insulin. In another embodiment, the present invention provides methods for the prevention, treatment or amelioration of one or more symptoms associated with a bone-reabsorption disease such as osteoporosis, metastatic bone cancer, osteolytic lesions with an orthopedic implant, Paget's disease, or bone loss associated with hyperparathyroidism, said methods comprising administering to an animal in need thereof an effective amount of a reverse micelle composition comprising one or more fatty acid esters or hydrophilic derivatives thereof, a stabilizer, a hydrophilic phase, and parathyroid hormone, calcitonin or an analog thereof. In accordance with these embodiments, the reverse micelle compositions comprise less than 15%, less than 10%, less than 5%, or less than 2% by weight of triester.

The present invention provides methods for diagnosing or monitoring the state of a disease or disorder, said methods comprising administering to said animal an effective amount of a reverse micelle composition comprising a surfactant, a hydrophilic phase, and one or more diagnostic agents useful in the diagnosis of said disease or disorder. In particular, the present invention provides methods for diagnosing or monitoring the state of a disease or disorder, said methods comprising administering to an animal an effective amount of a reverse micelle composition comprising a surfactant, a stabilizer, a hydrophilic phase, and one or more diagnostic agents useful in the diagnosis of said disease or disorder. In one embodiment, the present invention provides methods for diagnosing or monitoring the state of a disease or disorder, said methods comprising administering to an animal an effective amount of a reverse micelle composition comprising one or more fatty acid esters or hydrophilic derivatives thereof, a hydrophilic phase, a stabilizer, and one or more diagnostic agents useful in the diagnosis said disease or disorder. In accordance with this embodiment, the reverse micelle compositions comprise less than 15%, preferably less than 10%, less than 5%, or less than 2% by weight of triester. Preferably, the fatty acid esters of the reverse micelle compositions have a length of 6 to 12 carbon atoms. In another embodiment, the present invention provides methods diagnosing or monitoring the state of a disease or disorder, said methods comprising mucosally administering an animal an effective amount of a reverse micelle composition comprising monoglycerides, diglycerides- or hydrophilic derivatives thereof, a hydrophilic phase, a stabilizer, and one or more diagnostic agents useful in the diagnosis of said disease or disorder. In another embodiment, the present invention provides methods diagnosing or monitoring the state of a disease or disorder, said methods comprising mucosally administering to an animal an effective amount of a reverse micelle composition comprising monoglycerides or diglycerides or a mixture thereof, a hydrophilic phase, a stabilizer, and one or more diagnostic agents useful in the diagnosis of said disease or disorder, wherein the acyl groups of the monoglycerides or diglycerides are enriched in fatty acids having 6-8, 6-10, 6-12, 8-10, or 8-12 carbon atoms. In accordance with this embodiment, the monoglycerides or diglycerides may be partially derivatized with a hydrophilic moiety to provide polarity to increase water solubility. Preferably, the reverse micelle compositions administered to an animal comprise less than 15%, less than 10%, less than 5%, or less than 2% by weight of triglycerides.

The present invention provides kits comprising in an appropriate container(s) reverse micelle compositions comprising a surfactant, a stabilizer, a hydrophilic phase, and one or more biologically active molecules. In particular, the present invention provides kits comprising in an appropriate container(s) reverse micelle compositions comprising one or more fatty acid esters or hydrophilic derivatives thereof, a stabilizer, a hydrophilic phase, and one or more biologically active agents. Preferably, the reverse micelle compositions included in the kits of the invention comprise less than 15%, less than 10%, less than 5%, or less than 2% by weight of triester. The present invention also provides kits comprising reverse micelle compositions comprising monoglycerides, diglycerides, or hydrophilic derivatives thereof, a stabilizer, a hydrophilic phase, and one or more biological active molecules. The present invention further provides kits comprising in an appropriate container(s) reverse micelle compositions comprising monoglycerides or diglycerides or a mixture thereof, a stabilizer, a hydrophilic phase, and one or more biologically active molecules, wherein the acyl groups of the monoglycerides or diglycerides are enriched in fatty acids having 6-12 carbon atoms. The reverse micelle compositions included in the kits of the invention may comprise monoglycerides or diglycerides which are partially derivatized with a hydrophilic moiety to provide polarity to increase water solubility. Preferably, the reverse micelle compositions included in the kits of the invention comprise less than 15%, less than 10%, less than 5%, or less than 2% by weight of triglycerides.

The reverse micelle compositions of the invention included in kits may be formulated in a compatible pharmaceutical carrier. Preferably, the kits of the invention are accompanied by instructions for administration. The kits of the invention may further comprise a list of the diseases and/or disorders for which the reverse micelle compositions may be used to prevent, treat, diagnose or monitor.

The present invention provides kits comprising in one or more containers one or more reverse micelle compositions comprising a surfactant, a stabilizer, a hydrophilic phase, and one or more biologically active molecules, wherein at least one of the biologically active molecules is a protein, polypeptide or peptide. In a specific embodiment, the kits of the invention comprise one or more containers and one or more reverse micelle compositions comprising one or more fatty acid esters or hydrophilic derivatives thereof, a stabilizer, a hydrophilic phase, and one or more biologically active molecules, wherein at least one of the biologically active molecules is a protein, polypeptide or peptide. In accordance with this embodiment, the reverse micelle compositions included in the kits comprise less than 15%, less than 10%, less than 5%, or less than 2% by weight of triester. In particular, the present invention provides kits comprising reverse micelle compositions comprising hormones (e.g., luteinizing hormone-releasing hormone (LHRH), parathyroid hormone (PTH), calcitonin, insulin, and growth hormone) or agonists thereof (e.g., LHRH agonists) or low molecular weight heparins.

In a preferred embodiment, the kits of the invention comprise in one or more containers one or more reverse micelle compositions comprising one or more fatty acid esters or hydrophilic derivatives thereof, a stabilizer, a hydrophilic phase, and one or more LHRH agonists. In another preferred embodiment, the kits of the invention comprise in one or more containers reverse micelle compositions comprising one or more fatty acid esters or hydrophilic derivatives thereof, a stabilizer, a hydrophilic phase, and growth hormone, preferably human growth hormone. In another preferred embodiment, the kits of the invention comprise in one or more containers reverse micelle compositions comprising one or more fatty acid esters or hydrophilic derivatives thereof, a stabilizer, a hydrophilic phase, and parathyroid hormone or calcitonin. In yet another preferred embodiment, the kits of the invention comprise in one or more containers reverse micelle compositions comprising one or more fatty acid esters or hydrophilic derivatives thereof, a stabilizer, a hydrophilic phase, and insulin. In accordance with these embodiments, the reverse micelle compositions included in the kits comprise less than 15%, less than 10%, less than 5%, or less than 2% by weight of triester.

3.1 DEFINITIONS

As used herein the terms "hydrophilic phase" and "aqueous phase" refer to compounds which are miscible with water including, but are not limited to, water, glycerol, sorbitol, mannitol, propylene glycol, ethylene glycol, polyethylene glycol, buffering agents, tonicity agents, oxidizing agents, reducing agents, antimicrobial agents, preservatives and other stabilizing agents or mixtures thereof.

As used herein, the term "buffer solution" is defined as an aqueous solution or aqueous solution containing less than 25% of a miscible organic solvent, in which a buffer has been added to control the pH of the solution. Examples of suitable buffers include, but are not limited to, PBS (phosphate buffered saline), TRIS (tris-(hydroxymethyl) aminomethane), HEPES (hydroxyethylpiperidine ethane sulfonic acid), sodium phosphate and TES (2-[(tris-hydroxymethyl)methyl]amino-1-ethanesulfonic acid).

As used herein, the terms "mucosa" and "mucosal" refer to a mucous tissue such as epithelium, lamina propria, and a layer of smooth muscle in the digestive tract. "Mucosal delivery", "mucosal administration" and analogous terms as used herein refer to the administration of a composition to the mucosal tissue. Mucosal delivery", "mucosal administration" and analogous terms include, but are not limited to, the delivery of a composition the through bronchi, gingival, lingual, nasal, oral, vaginal, rectal, and intestinal mucosal tissue.

4. BRIEF DESCRIPTION OF THE FIGURES

FIG. 1 Pharmacokinetics of human growth hormone in rats following intraduodenal administration.

Figure 2:
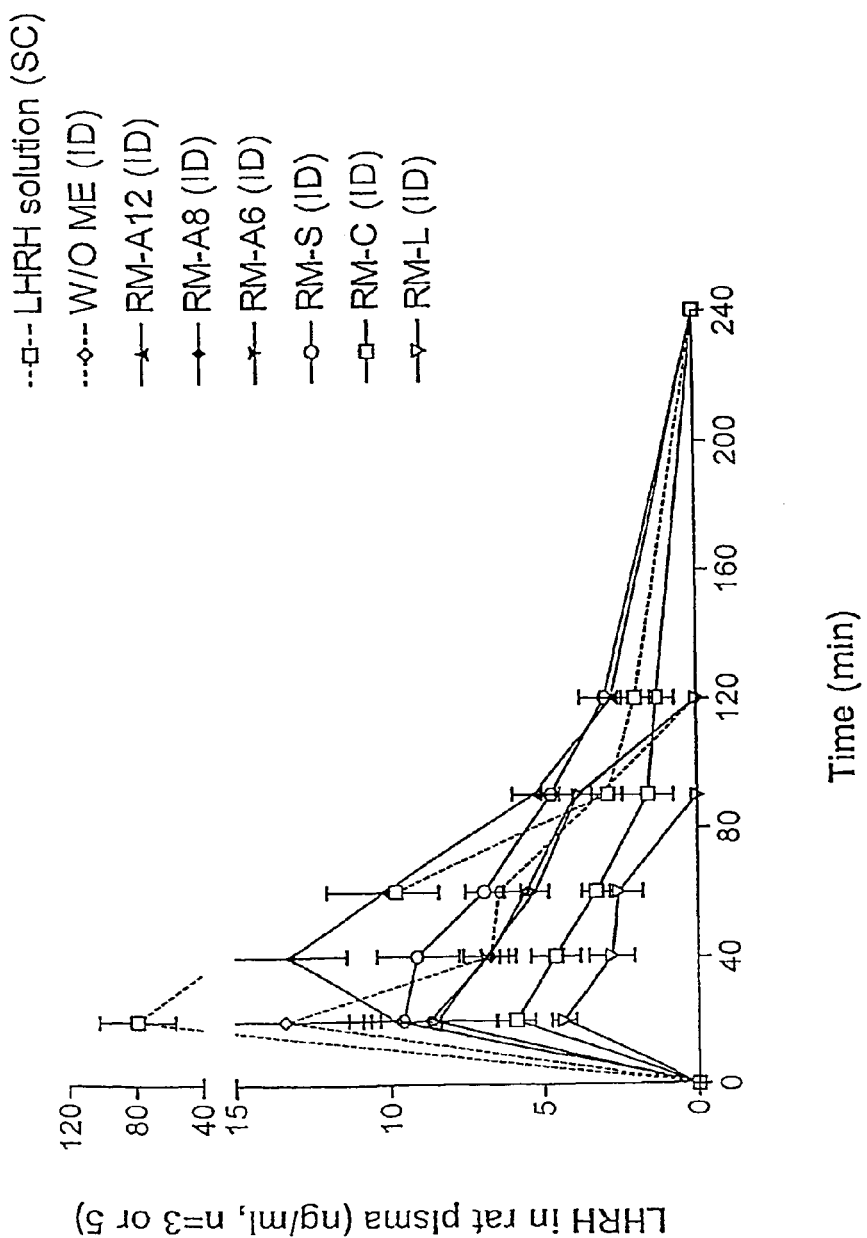

FIG. 2 Pharmacokinetics of LHRH in rats following intraduodenal administration.

Figure 3:
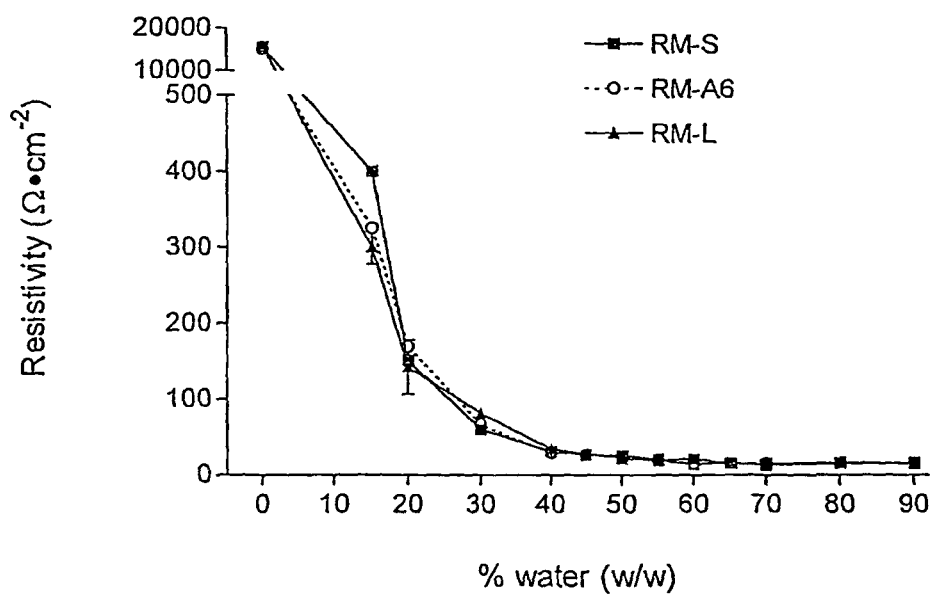

FIG. 3 Resistivity of various RM (Reverse Micelle) formulations containing electrolytes upon dilution with deionized water.

Figure 4:
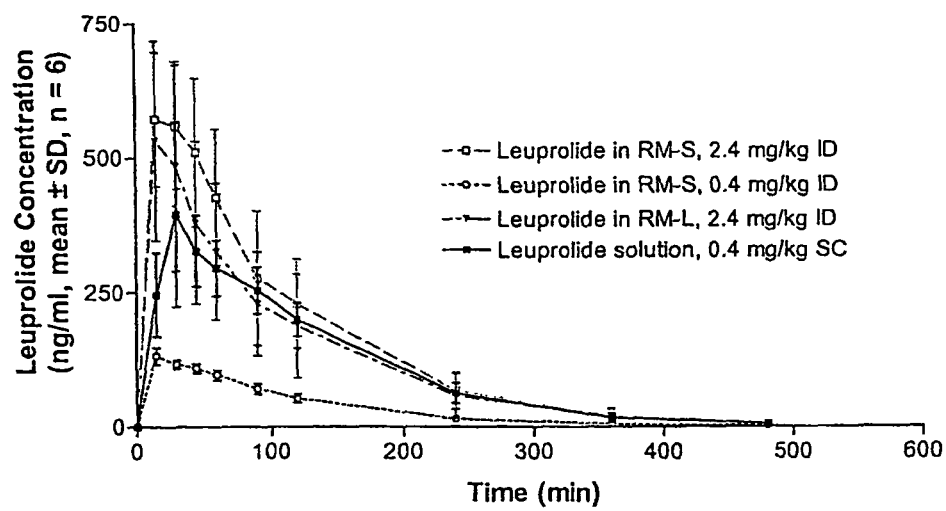

FIG. 4 Leuprolide plasma concentration profile in dogs following subcutaneous and intraduodenal administration.

5. DETAILED DESCRIPTION OF THE INVENTION

The present invention provides compositions and methods for the delivery of hydrophilic molecules and other poorly absorbed water-soluble molecules to an animal. In particular, the present invention relates to compositions and methods for the delivery of biologically active molecules, including hydrophilic and poorly absorbed water-soluble molecules. In accordance with the present invention, biologically active molecules include, but are not limited to, therapeutic agents, diagnostic agents, antigens, antibodies, peptides, polypeptides, viruses, nucleic acids, growth factors, cytokines, and drugs. The reverse micelle compositions of the present invention promote the absorption of biologically active molecules by mucosal tissues. The reverse micelle compositions of the invention also reduce the dosage of a biologically active molecule necessary to achieve a prophylactic or therapeutic effect, and thus, reduce the toxicity associated with administering higher dosages of certain biologically active molecules. Further, the reverse micelle compositions of the invention reduce dosage of a diagnostic agent necessary to diagnose or monitor the state of a disease or disorder.

The invention provides for reverse micelle compositions comprising a surfactant (e.g., a P-glycoprotein inhibitor), a hydrophilic phase and one or more biologically active molecules. In particular, the invention provides for reverse micelle compositions comprising a surfactant, a stabilizer, a hydrophilic phase and one or more biologically active molecules. Preferably, the reverse micelle compositions comprise less than 15%, less than 10%, less than 5%, or less than 2% by weight of triester. The invention also provides for reverse miceile compositions comprising one or more fatty acid esters or hydrophilic derivatives thereof, a stabilizer, a hydrophilic phase, and a biologically active molecule, wherein the reverse micelle compositions comprise less than 15%, preferably less than 10%, less than 5%, or less than 2% by weight of triester. Preferably, the reverse micelle compositions comprise fatty acid esters having fatty acids with a length of about 6 to about 12 carbon atoms. The present invention also provides reverse micelle compositions comprising monoglycerides, diglycerides or mixtures thereof, one or more stabilizers, a hydrophilic phase, and one or more biologically active molecules. Optionally, the reverse micelle compositions of the invention may combined with one or more pharmaceutically acceptable carriers, diluents or excipients.

The reverse micelle compositions of the invention may be used to administer a variety of biologically active molecules to prevent, treat, or ameliorate the symptoms associated with diseases or disorders. The reverse micelle compositions of the invention may also be used to administer a diagnostic agent to facilitate the diagnosis of a disease or a disorder. The invention provides methods for the delivery a biologically active molecule to an animal, said methods comprising administering to said animal an effective amount of a reverse micelle composition comprising a surfactant, a hydrophilic phase, and a biologically active molecule. In particular, the invention provides methods for the delivery a biologically active molecule to an animal, said methods comprising administering to said animal an effective amount of a reverse micelle composition comprising a surfactant, a stabilizer, a hydrophilic phase, and a biologically active molecule. The present invention also provides methods for administering a biologically active molecule to an animal, said methods comprising administering to said animal an effective amount of a reverse micelle composition comprising one or more fatty acid esters or hydrophilic derivatives thereof, a stabilizer, a hydrophilic phase and a biologically active molecule, wherein the reverse micelle compositions comprise less than about 10% by weight of triester, preferably about 5% by weight of triester. In a preferred embodiment of the invention, the reverse micelle compositions of the invention are administered mucosally to an animal as a capsule, soft elastic gelatin-capsule, caplet, aerosol, spray, solution, suspension, emulsion, cachet, tablet, capsule, soft elastic gelatin capsule, aerosol, powder or granule. Preferably, the reverse micelle compositions of the invention are administered to a mammal, more preferably a human to prevent, treat, diagnose or monitor a disease or disorder.

5.1 Reverse Micelles

The invention provides for the use of a single component surfactant micelle which avoids more complex mixtures of oils and surfactants, yet still allows for suitable transepithelial transport of biologically active molecules. The biologically active molecule is contained within the hydrophilic phase of a reverse micellar (L2) phase of a single type of surfactant or polar lipid. In particular, the present invention provides reverse micelle compositions comprising a surfactant, a hydrophilic phase and one or more biologically active molecules. In one embodiment, the reverse micelle compositions comprise a surfactant, a hydrophilic phase, and one or more biologically active molecules, wherein the surfactant is a P-glycoprotein. In another embodiment, the reverse micelle compositions of the invention comprise one or more fatty acid esters or hydrophilic derivatives thereof, a hydrophilic phase, and one or more biologically active molecules. Preferably, such compositions comprise less than about 15%, less than 10%, less than 5%, or less than 2% by weight of triester and the fatty acids in the fatty acid esters of the reverse micelle compositions have a length of 6 to 20 carbon atoms, more preferably 6 to 12 carbon atoms, most preferably 8 to 10 carbon atoms.

In a specific embodiment, the reverse micelle compositions of the invention comprise monoglycerides or diglycerides or a mixture thereof, a hydrophilic phase, and one or more biologically active molecules. In a preferred embodiment, the reverse micelle compositions of the invention comprise monoglycerides, diglycerides or mixtures thereof, a hydrophilic phase, and one or more biologically active molecules, wherein the acyl groups of the monoglycerides or diglycerides are enriched in fatty acids having 6-8, 6-10, 6-12, 8-10 or 8-12 carbon atoms. In accordance with this embodiment, the monoglycerides or diglycerides may be partially derivatized with a hydrophilic moiety to provide polarity to increase water solubility. Preferably, the reverse micelle compositions of the invention comprise less than 15%, less than 10%, less than 5%, or less than 2% by weight of triglycerides. Optionally, the reverse nicelle compositions of the invention may comprise buffering, oxidizing, reducing and/or tonicity agents in the hydrophilic phase to provide adequate solubility and stability of the biologically active molecule. In a preferred embodiment, the reverse micelle compositions of the invention further comprise a stabilizer.

In a specific embodiment, the hydrophilic phase of the reverse micelle compositions of the invention comprises an amount from about 0 to about 70%, about 0 to about 65%, about 0 to about 50%, about 0 to about 40%, about 0 to about 30%, about 0 to about 20%, about 5% to about 70%, about 5 to about 65%, about 5 to about 50%, about 5 to about 40%, about 5 to about 30%, about 5 to about 20%, about 5% to about 15%, or about 5% to about 10% by weight of the reverse micelle. In another embodiment, the hydrophilic phase of the reverse micelle compositions of the invention comprises an amount from 0 to 70%, 0 to 65%, 0 to 50%, 0 to 40%, 0 to 30%, 0 to 20%, 5% to 70%, 5 to 65%, 5 to 50%, 5 to 40%, 5 to 30%, 5 to 20%, 5% to 15%, or 5% to 10% by weight of the reverse micelle. In a preferred embodiment, the hydrophilic phase of the reverse micelle compositions of the invention comprises an amount from about 5% to about 25% by weight of the reverse micelle, more preferably 5% to 25% by weight of the reverse micelle. Examples of compounds which may be included in the hydrophilic phase of a reverse micelle composition of the invention include, but are not limited to, water, glycerol, sorbitol, mannitol, propylene glycol, ethylene glycol and polyethylene glycol or mixtures thereof. In a preferred embodiment, the hydrophilic phase of the reverse micelle compositions of the invention comprise water.

The surfactant incorporated in the reverse micelle compositions of the invention may be non-ionic in nature, that is having a neutral overall electrical charge, or ionic in nature, that is being positively or negatively charged without affecting the stability of the compositions. In a preferred embodiment of the invention, the surfactants incorporated in the reverse micelle composition are non-ionic in nature. The surfactant incorporated into a reverse miceule composition of the invention may be a single compound or a mixture of compounds. Preferably, the reverse micelle compositions of the invention only comprise one surfactant. Examples of surfactants include, but are not limited to, fatty acid esters and hydrophilic analogs thereof. In a preferred embodiment, the surfactant is one or more fatty acid esters or hydrophilic derivatives thereof. Preferably, the surfactant is: (1) monoglycerides or hydrophilic derivatives or analogs thereof; (2) diglycerides or hydrophilic derivatives or analogs thereof; or (3) a mixture of monoglycerides or hydrophilic derivatives or analogs thereof and diglycerides or hydrophilic derivatives or analogs thereof. In a specific embodiment, the surfactant incorporated in the reverse micelle compositions of the present invention is a P-glycoprotein inhibitor.

Fatty acid chain lengths of 8-10 carbon atoms enriched with monoglycerides, diglycerides and their polyoxyethylated analogs can, e.g., be derived from coconut oil by alcoholysis and transesterification reactions. In another method, these esters can be derived by direct esterification of glycerol using C8/C10 fatty acid esters in the presence of polyethylene glycol or ethylene oxide if so desired. The following medium chain fatty acid monoglycerides, diglycerides/polyoxyethylene esters are available commercially under different names as presented in Table 1 and can be used in the reverse micelle compositions of the invention.

TABLE 1

Medium chain fatty acid glycerol/polyoxyethylene esters

| Fatty acid Ester | Commercial name | Supplier |
|---|---|---|
| Glyceryl monocaprylate | Capmul MCM C-8 | Abitec |
| Glyceryl monocaprate | Capmul MCM C-10 | Abitec |
| Medium chain mono- and di-glycerides | Capmul MCM | Abitec |
| Polyoxyethylene 6 caprylic/capric glycerides | Acconon CC-6 | Abitec |
| Polyoxyethylene 12 capric/caprylic Glycerides | Acconon CC-12 | Abitec |
| Macrogol glycerol Capryl caproate | Acconon MC-8 | Abitec |
| Macrogol caprylic/capric glycerides | Labrasol | Gattefosse |
| Caprylic-capric Glycerides ethylene oxide ester | Softigen 767 | Sasol |
| Tartaric Acid mono- and di-glycerides | Imwitor 1327 GR | Sasol |
| Diacetyl tartaric acid monoglyceride | Imwitor 2020 | Sasol |
| Caprylic acid Monoglyceride | Imwitor 312 | Sasol |
| Caprylic/capric glycerides | Imwitor 742 | Sasol |
| Capric acid mono- and di-glycerides | Imwitor 988 | Sasol |
| Lactic acid mono- and di-glycerides | Imwitor 515S Imwitor 520S | Sasol |
| Caprylic/Capric triglycerides | Captex355 | Abitec |
|  | Miglyol 812 | Sasol |

For stable reverse micelle formation, the surfactant is generally chosen from unsubstituted or partially substituted monoglycerides and diglycerides having fatty acids with a length of 6-20 carbon atoms (C6-C20), preferably 6-12 carbon atoms, most preferably 8-10 carbon atoms. The most preferred substitution of the monoglycerides and diglycerides is ethoxylation or pegylation. Other suitable hydrophilic analogs of monoglycerides include, but are not limited, lactic acid, acetic acid, citric acid, succinic acid, and diacetyl tartaric acid esters. Typically the surfactant has an HLB value between about 1 and about 40, preferably between about 1 and about 20, most preferably between about 5 and about 20. Pegylated or polyglycolized glycerides are derived in the synthesis from a mixture of monoglycerides, diglycerides and triglycerides and polyethylene glycol (PEG) monoesters and diesters, usually with a molecular weight (MW) between 200 and 10,000 daltons, preferably between 200 and 4,000 daltons. The HLB value of the polyglycolized glycerides is adjusted by the length of the PEG chain and of the length and degree of saturation of the fatty acid substitutions. In a preferred embodiment of this invention, the surfactant is composed of C8-C10 substituted polyglycolized glycerides, having an BLB value less than 20 and preferably, between 5 and 15.

Reverse micelle compositions of the invention may be fabricated with a surfactant in which a biologically active molecule is functionally solubilized in the hydrophilic phase of the reverse micelle. Preferably, reverse micelle compositions of the invention are fabricated with chemically-modified monoglycerides or diglycerides in which the biologically active molecule is functionally solubilized in the hydrophilic phase of the reverse micelle. In certain embodiments, the hydrophilic moiety of the modified glyceride is a hydrophilic group, such as polyethylene glycol of various chain lengths. Medium chain fatty acid glyceride side chains are from 6-8, 6-10, 6-12, 6-20, 8-10, 8-12 or 8-20 carbons in length. The characteristics of the reverse micelle compositions can be modified and adjusted according to chemical conjugation of other surfactant active groups to the glyceride backbone. The resulting self-emulsifying systems are advantageous since they can be formed without the addition of oil and additional surfactant molecules.

5.2 Stabilizers

Reverse micelles prepared using the formulations of this invention can be modified or enhanced for delivery of biologically active molecules by improving stabilization upon dilution with water or contact with biological fluids. Accordingly, in order to stabilize the reverse micelle compositions against phase inversion, the reverse micelle compositions of the invention may comprise one or more stabilizers. Stabilizers may be chosen from monomeric compounds that are compatible with the hydrophobic or hydrophilic phase of the reverse micelles at elevated temperatures or when solubilized in organic solvents. Upon cooling or removal of the organic solvent such components form protective structures that can delay the phase transformation of the reverse micelle when diluted with water or in contact with bodily mucosal fluids. Stabilizers can also undergo interfacial polymerization at the interface between water and surfactant under conditions that do not damage biologically active molecules. Stabilizers include, but are not limited to, polymers that are compatible with the hydrophobic phase of the surfactant. Such polymers may be chosen from polymers that are hydrophobic or hydrophilic and can be added directly to the surfactant mixture or polymers that can be added in a solution of organic solvent that can subsequently be removed by evaporation. Further, polymers that can form microstructures such as microparticles, microtubules, microspheres, matrices, microcapsules and microcrystals that are compatible with the hydrophobic phase of the surfactant mixture may be used to stabilize the reverse micelle compositions. Such microstructures encapsulate the reverse micelle within their structure and delay the inversion of the reverse micelle when diluted in aqueous media or in contact with mucosal fluids. Thus, stabilizers include, but are not limited to, polymers that can coat the reverse micelle droplets, specifically gelatin microcapsules, that can protect the reverse micelle structures. Further, polymers that can form stable gels in the presence of the reverse micelle may be used. Examples of such polymers include, but are not limited to, polyacrylic acid crosslinked with either allylsucrose or allyl ethers of pentaerythritol. The gel formed thus delays the release of both the active compound and the surfactant.

A polymeric stabilizer may be a natural polymer, a synthetic polymer or a mixture thereof. Preferably, the polymeric stabilizer is a synthetic polymer. Examples of synthetic polymers include, but are not limited to, polylactide, poly-glycolide, a mixture of polylactide and polyglycolide, a hydrocarbon oligomer, a hydrocarbon polymer, a polycaprolactone, a polyorthoester, polysebacic acid, polyfumaric acid, a polyamide, a polycarbonate, a polyallylene, a polyacrylamide, poly(hydroxy acid), a polyanhydride, a polyorthoester and blends and copolymers thereof. In a preferred embodiment, the polymer is formed from a polymerizable fatty acid monomer or derivative, by interfacial ionic polymerization with water, by condensation of cyanoacrylates, including alkylcyano acrylates, or from condensation of ethyl 2-cyanoacrylate.

Stabilization can be achieved by forming biologically active molecule-containing micelles in the presence of monomeric polymerizable compounds and subsequent polymerization in situ. Polymerization in situ results in a polymer network surrounding the central hydrophilic drug-containing core. Alternatively, stabilization of reverse micelles can be achieved by the addition of hydrophobic polymers that interact with the hydrophobic moieties of the micelle-forming materials. The polymeric materials add physical rigidity to the system by interacting with acyl side chains of the micelle-forming material preventing the rapid phase transformation from reverse micelle (L2) to simple micelles (L1) or other phase. In a preferred embodiment, increased micellar stability is achieved by including polymerizable fatty acids with polyethylene glycol polar head groups. In another embodiment, fatty acids that have side chains that are polymerizable are co-polymerized as reverse micelles in conjunction with mono- and/or di-glycerides with medium chain fatty acid side chains. Such reverse micelles have greater stability in vitro upon contact with water or simulated or actual gastrointestinal fluid.

5.2.1 Polymerizable Fatty Acids and Interfacial Polymerization

U.S. Pat. No. 6,187,335 describes polymerizable fatty acid compounds. These compounds are aliphatic fatty acids with polymerizable groups in the head group or in the aliphatic chain. Such fatty acids are further modifiable by extension of their hydrophilic head groups by ethylene glycol addition or addition of other hydrophilic groups. The structure of these fatty acids gives them unique functionality and particular utility when used in conjunction with reverse micelles. The surfactant group is disposed between the polymerizable group and the functional acid group. The functional acid group can be optionally omitted. The surfactant group serves several functional purposes. The length of the polymeric chain of the surfactant group can be chosen to be short, medium or long, and the relative hydrophilicity/hydrophobicity of the chain can be altered. A long-chain surfactant group with significant hydrophilicity, for example, can provide hydrophilic groups that interact effectively with compounds that are dissolved in the reverse micellar hydrophilic phase.

For the purpose of forming polymers in situ in reverse micelles, polymerization of the fatty acid polymerizable moiety can be carried out by methods well-known to one of skill in the art. For example, unsaturated fatty acid compounds in the reverse micelle can be polymerized using three methods: (1) by actions of chemical initiators, e.g., redox pairs; (2) by physical excitations including sensitized photoinitiation, e.g., broad band ultraviolet (UV) or UV 254 nm or WV 302 nm irradiation, gamma-ray irradiation, cyanine dye with an argon laser; and (3) by the combination of both, e.g., chemical initiators with WV 365 nm irradiation. Diene polymerizable functions may be polymerized by exposure to short-wave or mid-wave ultraviolet light. Ultraviolet light at 302 nm may be used to polymerize diene function and the damage to biological molecules (e.g. proteins and peptides) can be minimized. Phenylacetophenone initiators combined with UV 365 nm irradiation has been used extensively in the polymerization of alkeno functionalities, such as acrylated PEG hydrogel for biomedical and molecular imprinting applications, polymethacrylate polymers for biomaterials and tissue engineering, and styrene/acrylate/methacrylate nanoparticles for drug delivery. Preferably, the amount of polymerization is from about 1% to about 95% at 365 nm, more preferably from about 5% to about 40% at 365 nm, most preferably from about 10% to about 20% at 365 nm.

Precise control of polymerization level is sometimes difficult to achieve with the use of chemical initiators, especially when low level of polymerization is needed, normally requiring additional steps to separate any unreacted initiators. Some processes may even result in harsh environment changes such as large pH drops and inactivation of protein drugs. As a result, the most desirable method is one where polymer can be controlled and active therapeutic materials can be fully retained. Thus, when utilizing ultaviolet light for polymerization, preferably, the wavelength of the ultraviolet light is of a long-range wavelength (UV band A), such as from about 320 nm to about 400 nm, and more preferably, the ultraviolet light is from about 350 nm to about 370 nm. Long range UV wavelengths are usually outside of the absorption range of proteins and, thus do not cause damage to proteinaeous molecules (e.g., proteins, polypeptides or peptides).

Co-polymerization of polymerizable fatty acids with reverse micelle compositions results in stabilized reverse micelles that undergo slower phase transformation in contact with bodily fluids found in the gastrointestinal tract, simulated fluids, or water. Such modified micelles are made by mixing aqueous solutions of active compounds with mixture of monoglycerides or diglycerides with polymerizable fatty acids, followed by polymerization of the fatty acid by ultraviolet light at a wavelength that does not cause damage to the biologically active molecules. Preferably, the wavelength of the ultraviolet light is of a long-range wavelength (UV band A), such as from about 320 nm to about 400 nm. More preferably, the wavelength of the ultraviolet light is from about 350 nm to about 370 nm. The fatty acids described are fully compatible with the amphiphilic micelle-forming materials and when contacted with water form thermodynamically stable reverse micelles with the polar head groups of the fatty acid forming the outer shell of the aqueous interior compartment. Polymerization of the fatty acids results in reverse micelles in which the fatty acid polymer stabilizes the monoglyceride or diglyceride ester reverse micelles. A variety of polymerizable fatty acid compounds can be used in this invention, including, but not limited to: 2,4-octadecadienoic acid [ODA], 2,4-octadecadienoyl-polyethylene glycol (200-4000) [ODP], 2,4 octadecadienoyl-PEG (200-4,000)-succinic acid [OPS], Bis-(2,4-octadecadienoyl)-polyethylene glycol (200-10,000) [BODP] and analogs thereof. Appropriate analogs include, but are not limited to, analogs modified by single amino acids or polypeptide chains, imido groups, polyamines, polyimines, polysaccharides, polyacids and polymers or co-polymers of propylene glycol and ethylene glycol. Other polymerizable moieties may also be used, including, but not limited to, conjugated dienes of C6-C24, conjugated diynes of C6-C24, and methacrylate modified or sulfhydryl-containing polar groups or hydrophobic tails of the fatty acids. The use of 2,4-conjugated dienes results in polymers that are linked to adjacent acyl groups close to the internal aqueous phase, where use of sulfhydryl containing polymerizable fatty acids results in head group polymerization at the interface of the aqueous and hydrophobic phases. In addition, other polymerizable fatty acid derivatives can be used to stabilize reverse micelles. The polar head group, for example, can consist of amino acids, polypeptides, polysaccharides, polyols, polyacrylic acids, polyimines, choline, peptidoglycols, glycopeptides, or other hydrophilic polymers with multiple positive or negative charges. Further, compounds that are polymerizable fatty acid derivatives of glycerol or glyceryl phosphatidyl derivatives compatible with reverse micelles can be used.

Monomeric compounds that can undergo polymerization in contact with water can be used to create polymers at the interface of the aqueous phase and the hydrophobic phase. Like polymerizable fatty acids, appropriate monomers include, but are not limited to, members of the cyano-acrylate family. For example, ethylcyanoacrylate can be dissolved in an organic solvent such as methylene chloride. A solution of ethyl 2-cyanoacrylate (ECA) dissolved in methylene chloride can be added to a preformed reverse micelle formed from a mixed C8-C10 monoglyceride diglyceride mixture containing an aqueous compartment. Upon stirring, ECA contacts the aqueous phase and polymerization is initiated. The removal of solvent by evaporation results in polymerization of ECA into a polymer principally at the interface of the monoglyceride diglyceride ester water interface.

5.2.2 Hydrophobic Polymers

Many polymers that are insoluble in water are soluble in organic solvents and can be added to mono- or di-glyceride fatty acid esters and/or their hydrophilic derivatives. Such polymers include, but are not limited to, polylactic acid, polyglycosides, polyortho ester, poly ebacic acid, polymethyl methacrylate, polyacretate, polystyrines, and polyfumarate. A preformed reverse micelle made with a mono- and/or di-glyceride can be directly mixed with a solution of polymer dissolved in a suitable organic solvent. By using essentially hydrophobic polymers, chains of polymers interact primarily with the hydrophobic side chain of the mono- or di-glyceride fatty acid ester and form a loose network of polymer chains. A loose network of polymer chains physically restrains the reverse micelle in contact with bodily fluids so that phase transformation is delayed. Preformed polymeric particles can also be used. These particles are suspended in an organic solvent and mixed with reverse micelles.

Alternatively, other lipidic compounds can be used to interact with hydrophobic fatty acid side chains of the mono- and/or di-glyceride fatty acid ester. Suitable compounds include, but are not limited to, low melting temperature waxes, including N.F. White Beeswax, Soy wax, Carnuba wax, Castor wax, Microwax, and other such waxes. Such waxes can be melted and mixed directly with mono- and/or di-glyceride fatty acid esters. The resulting mixtures are reverse micelles with gel-like properties, wherein the internal aqueous phase delays phase transformation in further contact with water.

5.2.3 Hydrophilic Polymers

Hydrophilic polymers may also be used as stabilizers. Such polymers can either remain in the aqueous phase of the reverse micelle, form a gel with the reverse micelle, or form a coating on the surface of the reverse micelle droplets. Suitable hydrophilic polymers include, but are not limited to, gelatin, polyacrylic acid cross-linked with either allylsucrose or allyl ethers of pentaerythritol, carrageenan and chitosan.

5.3 Biologically Active Molecules

The reverse micelles of the present invention may be utilized for the delivery of a wide variety of biological active molecules. As used herein, the term "biologically active molecule" and analogous terms refer to eukaryotic and procaryotic cells, viruses, vectors, proteins, peptides, polypeptides, nucleic acids (e.g., DNA and RNA nucleotides including, but not limited to, antisense nucleotide sequences, triple helices and nucleotide sequences encoding biologically active proteins, polypeptides or peptides), saccharides, polysaccharides, carbohydrates, lipids, glycoproteins, and combinations thereof, and synthetic organic drugs and inorganic drugs exerting a biological effect when administered to an animal. In a preferred embodiment, biologically active molecules have an aqueous solubility of greater than 0.1 mg/ml, preferably greater than 1 mg/ml. Examples of biologically active molecules include, but are not limited to, anti-angiogenesis factors, antibodies (e.g., monoclonal antibodies, scFvs and Fab fragments), antigens (e.g., viral, microbial or tumor-associated antigens), growth factors, hormones, enzymes, peptides (preferably, peptides with a molecular weight (MW) from about 500 to about 10,000 daltons, more preferably with a MW from about 500 to about 5,000 daltons), drugs (e.g., steroids, anti-cancer drugs such as chemotherapeutic agents, antiviral agents, anti-inflammatory agents and antibiotics), insecticides, insect repellents, fertilizers, vitamins, or any other material having a biological effect. The reverse micelle compositions of the invention may be engineered to contain a biologically active molecule derived from the same or different species as the recipient of the reverse micelle composition Preferably, the biologically active molecule incorporated into a reverse micelle composition is derived from the same species as the recipient of the reverse micelle composition. Thus, in a preferred embodiment, a reverse micelle composition containing a biologically active molecule derived from a human is administered to a human.

The reverse micelles compositions of the invention have utility for the mucosal delivery of a wide variety of vaccines and/or antigens. For example, the reverse micelles compositions of the present invention may be designed to carry a wide variety of antigens including, but not limited to, diphtheria toxoid, tetanus toxoid, ospA antigen from Lyme disease bacterium, HTLV-1 or HTLV-2 antigens (e.g., HTLV-1 envelope protein or an antigenic fragment thereof), influenza virus antigens (e.g., influenza virus hemagglutinin or an antigenic fragment thereof), polio virus antigens, rhinovirus antigens, rabies virus antigens, vaccinia virus antigens, Epstein-Barr virus antigens, hepatitis virus antigens, HIV-1 and HIV-2 antigens (e.g., glycoprotein 120 or fragment thereof), and herpes virus antigens. The reverse micelle compositions may be engineered to contain an antigen derived from any species.

The reverse micelle compositions of the invention may also be utilized for the mucosal delivery of a wide variety of prophylactic or therapeutic agents. As used herein, the term "prophylactic agents" and analogous terms refer to biologically active molecules which can be used to prevent the onset, development or progression of one or more symptoms of a disease and/or disorder. As used herein, the term "therapeutic agent" and analogous terms refer to biologically active molecules which can be used to treat or ameliorate one or more symptoms associated with a disease and/or a disorder. Examples of therapeutic agents include, but are not limited to, chemotherapeutic agents, antibiotics, cytokines, hormones, enzymes (e.g., superoxide dismutase, asparaginase, arginase, arginine deaminase, adenosine deaminase, ribonuclease, trypsin, chymotrypsin and papain), tachykinin receptor agonists and antagonist peptides, vasoactive intestinal peptide, calcitonins, vasopressins, growth hormone releasing peptide, luteinizing hormone-releasing hormone (LHRH) agonists, fibrinogen receptor antagonists (RGD peptides see, e.g., the RGD peptide described in International Publication No. WO 93/02664) having in their sequence arginine-glycine-D-aspartic acid), fertility drugs, antiviral agents (e.g., ddI, AZT, ddC, acyclovir and the like), antibacterial agents, antifungal agents, and DNA and RNA nucleotides (including antisense nucleotide sequences, triple helices and nucleotide sequences encoding proteins, polypeptides or peptides). Examples of chemotherapeutic agents include, but are not limited to, arabinofuranosyladenine, acylguanosine, Nordeoxyguanosine, dideoxyadenosine, dideoxycytidine, dideoxyinosine Floxuridine, 6-mercaptopurine, doxorubicin, Daunorubicin, I-darubicin, quinidine, cisplatin, carboplatin, epirubicin, leuprolide, goserelin, nafarelin, histrelin, bicalutamide, goserelin, nafarelin, irinotecan, gemcitabine, and sargramostim. The peptides described in International Publication No. WO 93/02664 are incorporated herein by reference, in particular the peptides described on pages 10-12.

Examples of antibiotics include, but are not limited to, aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-alpha, IFN-beta, and IFN-gamma). Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

In a preferred embodiment, a reverse micelle composition of the invention comprises LHRH or an analog thereof. In another preferred embodiment, a reverse micelle composition of the invention comprises LHRH agonists such as leuprolide, goserelin, nafarelin and histrelin. In another preferred embodiment, a reverse micelle composition of the invention comprises parathyroid hormone or calcitonin. In another preferred embodiment, a reverse micelle composition of the invention comprises insulin. In a still further preferred embodiment, a reverse micelle composition of the invention comprises human growth hormone or an analog thereof. Preferably, the amount of biologically active molecule included in the reverse micelle composition is from about 0.05 to about 100 mg/ml, more preferably from about 0.05 to about 50 mg/ml, and most preferably from about 0.05 to about 10 mg/ml.

For ease of reference, the term "biologically active molecule" is also used herein to include diagnostic agents. Examples of diagnostic agents include, but are not limited to, radio-opaque compounds, magnetic compounds, fluorescent compounds, radioactive compounds, and other contrast agents used with ultrasound, x-rays, fluorescence, MRI, CT, and other techniques known to those skilled in the art. Formulation of these materials is typically critical for effective delivery, detection sensitivity, targeting to an intended site, and for improved comfort to the patient.

5.4 Modes of Administering Reverse Micelle Compositions to an Animal

The reverse micelle compositions are particularly suitable for delivery through mucosal tissue or epithelia. Accordingly, the reverse micelle compositions of the present invention are preferably administered by those routes which optimize uptake by mucosa, for example, oral, sublingual, buccal, rectal and intranasal routes of administration. However, topical, transdermal and parenteral delivery may also be used. The most preferred route of administration of the reverse micelle composition is oral administration. The reverse micelle compositions of the invention can be delivered orally in the form of tablets, capsules, cachets, gelcaps, solutions, suspensions and the like. Oral dosage forms may further fabricated to release the biologically active molecules at different regions of the GI tract, such as the small intestine and the colon, and in a time-dependent manner. When the dosage unit form of the reverse micelle composition comprising an antigen is a capsule, it can contain, in addition to the material of the above type, a liquid carrier or adjuvant. If administered topically the reverse micelles will typically be administered in the form of an ointment, cream or transdermal patch. If administered intranasally the reverse micelle composition will typically be administered in an aerosol form, spray, mist or in the form of drops. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

The reverse micelle compositions of the present invention are suitable for administration to animals, in particular domestic animals and birds, and more particularly humans. For example, domestic animals such as dogs and cats, as well as domesticated herds, cattle, sheep, pigs and the like may be treated or vaccinated with the reverse micelle compositions of the present invention. In a preferred embodiment, the reverse micelle compositions of the present invention are administered to humans.

In one embodiment, a reverse micelle composition of the present invention comprising two or more biologically active molecules may be administered to an animal in need thereof. Preferably, the biologically active molecules incorporated in the reverse micelle compositions of the invention act together additively or synergistically to achieve the desired biological effect In another embodiment, two or more reverse micelle compositions containing the same biologically active molecule may be administered to an animal in need thereof simultaneously or separately. In another embodiment, two or more reverse micelle compositions comprising one or more different biologically active molecules may be administered to an animal in need thereof simultaneously or separately.

Reverse micelle compositions are generally provided in a hermetically sealed container such as an ampule or sachet, and stored at room temperature or 4° C. The reverse micelle compositions of the invention may be provided in the form of tablets, capsules, cachets, gelcaps, solutions, suspensions and the like. The reverse micelle compositions of the invention may further be lyophilized into a fine powder which can be distributed in the form of a capsule or other suitable dosage form. The maximum amount of water that can be used in the reverse micelles in a capsule depends on the type and property of the capsules. Reverse micelles having lower water contents are normally more-compatible with gelatin capsules. In a specific embodiment, reverse micelles used in LiCaps gelatin capsules from CAPSUGEL have a water content by weigh of 0 to about 70%, about 0 to about 65%, about 0 to about 50%, about 0 to about 40%, about 0 to about 30%, about 0 to about 20%, about 0 to about 15%, about 0 to about 10%, about 5 to about 70%, about 5 to about 60%, about 5 to about 50%, about 5 to about 40%, about 5 to about 30%, about 5 to about 20% about 5 to about 15%, or about 5 to about 10%. In a preferred embodiment, reverse micelles used in LiCaps gelatin capsules from CAPSUGEL have a water content by weight of about 0 to about 40%. In another preferred embodiment, reverse micelles used in LiCaps gelatin capsules from CAPSUGEL have a water content by weigh of about 0 to about 30%. In a more preferred embodiment, reverse micelles used in LiCaps gelatin capsules from CAPSUGEL have a water content by weigh of about 0 to about 20%. In a most preferred embodiment, reverse micelles used in LiCaps gelatin capsules from CAPSUGEL have a water content by weigh of about 0 to about 15%. The compatibility of the reverse micelles with capsules can be changed by a modifier, for example a gelling agent, in the reverse micelles to reduce the interaction of water with the inner capsule wall, by applying coatings on the inner surface of the capsules, or by changing the storage conditions such as lowering the storage temperature.

Dosages (i.e., the effective amount—the amount of the composition sufficient to result in a desired therapeutic effect, such as treatment, prevention or amelioration of one or more symptoms of a disease or disorder) of the reverse micelle compositions will vary depending on the individual patient, the mode of administration, and the type and severity of the disease or disorder. Preferably, the dosage of the reverse micelle composition is from about 0.1 to about 1000 mg/kg, more preferably from about 0.1 to about 100 mg/kg, and most preferably from about 0.1 to about 50 mg/kg. Such dosages can be determined by a skilled physician using standard techniques.

The reverse micelle compositions can be used to prevent, treat or diagnose many diseases and/or disorders including, but not limited to, cancer, infectious diseases, and immune disorders (e.g., autoimmune disorders, asthma, and allergies). In a specific embodiment, the present invention provides methods for the prevention, treatment or amelioration of one or more symptoms associated with prostate cancer, endometriosis, precocious puberty, uterine lelomyotama, fertility disorder, premenopausal breast cancer, endometiral cancer, ovarian cancer, benign prostatic hypertrophy, functional bowel disease, cluster headache, premensual syndrome, idiopathic hirsuitism, hirsuitism second to polycycstic ovarian disease, adenomyosis, Meniere's disease, sickle cell anaemia associated priapism or catamental pneumothorax., said methods comprising administering to an animal in need thereof an effective amount of a reverse micelle composition comprising one or more fatty acid esters or hydrophilic derivatives thereof, a stabilizer, a hydrophilic phase, and one or more LHRH agonists. In another embodiment, the present invention provides methods for the prevention, treatment or amelioration of one or more symptoms associated with hypopituitarism, hypothyroidism, human growth hormone deficiency, Cushing's syndrome, nutritional short stature, intrauterine growth retardation, Russell Silver syndrome or achondroplasia, said methods comprising administering to an animal in need thereof an effective amount of a reverse micelle composition comprising one or more fatty acid esters or hydrophilic derivatives thereof, a stabilizer, a hydrophilic phase, and growth hormone, preferably human growth hormone. In another embodiment, the present invention provides methods for the prevention, treatment or amelioration of one or more symptoms associated a bone-reabsorption disease such as osteoporosis, metastatic bone cancer, osteolytic lesions with an orthopedic implant, Paget's disease, or bone loss associated with hyperparathyroidism, said methods comprising administering to an animal in need thereof an effective amount of a reverse micelle composition comprising one or more fatty acid esters or hydrophilic derivatives thereof, a stabilizer, a hydrophilic phase, and parathyroid hormone or calcitonin. In another embodiment, the present invention provides methods for the prevention, treatment or amelioration of one or more symptoms associated with diabetes, said methods comprising administering to an animal in need thereof an effective amount of a reverse micelle composition comprising one or more fatty acid esters or hydrophilic derivatives thereof, a stabilizer, a hydrophilic phase, and insulin. In accordance with these embodiments, the reverse micelle compositions comprise less than 15%, less than 10%, less than 5%, or less than 2% by weight of triester.

The reverse micelle compositions of the invention can be administered to an animal in combination with any known or currently used treatments for the prevention, treatment or amelioration of one or more symptoms associated with a particular disease or disorder. For example, a reverse micelle composition of the invention comprising a chemotherapeutic agent can be administered to animal with cancer in combination with radiation therapy.

5.5 Vaccine Formulations

In certain embodiments, the reverse micelle compositions comprise one or more antigens for use as vaccines. The vaccine formulations of the invention comprise a reverse micelle composition of the invention. Suitable preparations of vaccines formulations include, but are not limited to, liquid solutions or suspensions; solid forms such as capsules and tablets, and liquids for injections. The active immunogenic ingredients incorporated into the vaccine formulations of the invention are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Antigens may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium, potassium, ammonium, calcium, or ferric hydroxides, and such organic bases as isopropylamine, trimethylamine, 2-ethylamino ethanol, histidine, procaine and the like.

The vaccine formulations of the invention comprise an effective amount of a reverse micelle composition and a pharmaceutically acceptable carrier or excipient. Pharmaceutically acceptable carriers are well-known in the art and include, but are not limited to, saline, buffered saline, dextrose, water, glycerol, sterile isotonic aqueous buffer, and combinations thereof. One example of such an acceptable carrier is a physiologically balanced salt solution containing one or more agents such as stabilized, hydrolyzed proteins, lactose, etc., which serve to prevent degradation of the vaccine formulation. The carrier used in the vaccine formulation is preferably sterile and the formulation should suit the mode of administration. The vaccine formulations of the invention, if desired, can also contain minor amounts of wetting or emulsifying agents, or pH buffering agents. The vaccine formulation can be a liquid solution, suspension, emulsion, tablet, pill, capsule, sustained release formulation, or powder. Vaccine formulations for oral administration can include standard carriers such as pharmaceutical grades of mannitol, lactose, starch, magnesium stearate, sodium saccharine, cellulose, magnesium carbonate, etc.

Generally, the vaccine formulations are provided in a hermetically sealed container such as an ampule or a sachet. The vaccine formulations are generally stored at room temperature or 4° C. prior to use. The reverse micelle compositions of the invention may be lyophilized into a fine powder which can be distributed in the form of a capsule or other suitable dosage form.

The vaccine formulations of the invention may be multivalent or univalent. Many methods may be used to introduce the vaccine formulations of the invention; these include, but are not limited to, oral, intradermal, intramuscular, intraperitoneal, intravenous, subcutaneous, intranasal, topical, rectal, and via scarification (scratching through the top layers of skin, e.g., using a bifurcated needle). The patient to which the vaccine is administered is preferably an animal, more preferably a mammal, most preferably a human.

The precise dose of vaccine formulation to be employed will depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine formulations can be carried out by standard methods. For example, the purified protein(s) should be adjusted to an appropriate concentration, formulated with any suitable vaccine adjuvant and encapsulated within the reverse micelle. Suitable adjuvants may include, but are not limited to: mineral gels, e.g., aluminum hydroxide; surface active substances such as lysolecithin or pluronic polyols; polyanions; peptides; oil emulsions; alum, Lipid A and derivatives of Lipid A (e.g., monophosphoryl lipid A (MPLA)), cytokines, N-acetyl-murmyl-L-threonyl-D-isoglutamine (thr-MDP), N-acetylmuramyl-L-alanyl-D-isoglutamine, N-acetylmuramyl-L-isoglutaminyl-L-alanine-2(1',2'-dipalmitoyl-sn-glycero-3-hydroxyphosp horyloxy)-ethylamine, saponins, and microbial toxins (e.g., cholera toxin and heat labile toxin) and genetically altered derivatives thereof.

Effective doses (immunizing amounts) of the vaccines of the invention may also be extrapolated from dose-response curves derived from animal model test systems.

The present invention thus provides a method of immunizing an animal, or treating or preventing various diseases or disorders in an animal, comprising administering to the animal an effective immunizing dose of a vaccine formulation of the present invention.

5.6 Kits

The present invention provides kits comprising in an appropriate container(s) a reverse micelle composition comprising a surfactant, a hydrophilic phase, and one or more biologically active molecules. The present invention also provides kits comprising in an appropriate container(s) a reverse micelle composition comprising a surfactant, a stabilizer, a hydrophilic phase, and one or more biologically active molecules. The present invention also provides kits comprising in an appropriate container(s) reverse micelle compositions comprising one or more fatty acid esters or a hydrophilic derivative thereof, a stabilizer, a hydrophilic phase, and one or more biologically active agents. In one embodiment, kits comprise in an appropriate container(s) reverse micelle compositions comprising monoglycerides, diglycerides, or a hydrophilic derivative thereof, a stabilizer, a hydrophilic phase, and one or more biologically active molecules. In another embodiment, kits comprise in an appropriate container(s) reverse micelle compositions comprising monoglycerides, diglycerides, or a hydrophilic derivative thereof, a stabilizer, a hydrophilic phase, and different biologically active molecules. In another embodiment, kits comprise reverse micelle compositions comprising monoglycerides or diglycerides or a mixture thereof, a stabilizer, a hydrophilic phase, and one or more biologically active molecules, wherein the acyl groups of the monoglycerides or diglycerides are enriched in fatty acids having 6-12 carbon atoms. In accordance with this embodiment, the monoglycerides or diglycerides may be partially derivatized with a hydrophilic moiety to provide polarity to increase water solubility. Preferably, the reverse micelle compositions included in the kits of the invention comprise less than 15%, less than 10%, less than 5%, or less than 2% by weight of triglycerides. The reverse micelle compositions of the invention may be formulated in a compatible pharmaceutical carrier. Preferably, the kits of the invention are packaged with instructions for methods of administering a reverse micelle composition of the invention to an animal. The kits of the invention may also comprise a list of the diseases and/or disorders for which the compositions may be used to prevent, treat, diagnose or monitor.

5.7. Use of Antibodies Generated by the Reverse Micelle Compositions of the Invention Antibodies generated against an antigen by immunization of an animal (e.g., a mouse, rat, rabbit, monkey, etc.) with a reverse micelle composition of the invention comprising an antigen are useful in diagnostic immunoassays, passive immune therapy, and generation of antiidiotypic antibodies.

The generated antibodies may be isolated by standard techniques known in the art (e.g., immunoaffinity chromatography, centrifugation, precipitation, etc.) and used in diagnostic immunoassays. The antibodies may also be used to monitor treatment and/or disease progression. Any immunoassay system known in the art may be used for this purpose including, but not limited to, competitive and noncompetitive assay systems using techniques such as radioimmunoassays, ELISAs (enzyme-linked immunosorbent assays), "sandwich" immunoassays, precipitin reactions, gel-diffusion precipitin reactions, immunodiffusion assays, agglutination assays, complement-fixation assays, immunoradiometric assays, fluorescent immunoassays, protein A immunoassays and immunoelectrophoresis assays.

The reverse micelle compositions of the invention can also be used to produce antibodies for use in passive immunotherapy, in which short-term protection of an animal is achieved by the administration of a pre-formed antibody directed against a heterologous antigen.

The antibodies generated by the reverse micelle compositions of the invention can also be used in the production of antiidiotypic antibody. The antiidiotypic antibody can then in turn be used for immunization, in order to produce a subpopulation of antibodies that bind the initial antigen of the pathogenic microorganism (Jeme et al. *Ann. Immunol.* 125c:373, 1974; Jerne et al. *EMBO J.* 1:234, 1982).

In immunization procedures, the amount of immunogen to be used and the immunization schedule will be determined by a physician skilled in the at and will be administered by reference to the immune response and antibody titers of the animal.

The following examples are presented by way of illustration and not by way of limitation of the scope of the invention.

6. EXAMPLE

Reverse Micelles Containing Human Growth Hormone

This example demonstrates that reverse micelle compositions increase the bioavailability of biologically active molecules.
Preparation of Reverse Micelles
A solution of human growth hormone ("hGH") was prepared by dissolving purified human growth hormone in water. A reverse micelle was obtained by mixing the aqueous solution of human growth hormone with Acconon CC-12 in a 5:95 ratio (water to surfactant). Subsequently, the mixture was mixed well by vortexing and a transparent dispersion was obtained, indicative of stable reverse micelle formation. It will be appreciated by the skilled artisan that any mixing method known in the art that can disperse two phases can be used to prepare the reverse micelle compositions of the invention. The reverse micelle was stable upon storage at 4° C. and room temperature.
Bioavailability of hGH Following Intraduodenal Administration in Rats.
Sprague-Dawley rats (approximately weighing 120 grams each) were catheterized surgically with jugular and duodenal catheters. Each group of rats, 3-5 animals per group, received 600 micrograms of human growth hormone in Acconon CC-12 reverse micelle formulation or control formulations consisting of aqueous growth hormone or Acconon CC-12 water reverse micelle. Blood samples were obtained from the jugular catheter at the indicated times after administration. Plasma samples were obtained from the collected blood specimens and analyzed for the presence of hGH by an enzyme-linked immunosorbent assay (ELISA) (Alexon-Trend, BioCheck). The assay system utilizes polyclonal sheep anti-hGH for solid phase (microwells) immobilization, and mouse monoclonal anti-hGH in the antibody-enzyme (horseradish peroxidase) conjugate solution. The test serum or formulation sample was allowed to react simultaneously with the coated and conjugated antibodies, resulting in the hGH molecule being sandwiched between the solid phase and enzyme-linked antibodies. After a 45-minute incubation at room temperature, the sample well was washed to remove unbound enzyme labeled antibody. A solution of 3,3',5,5'-Tetramethylbenzidine (TMB) was added and incubated for 15 minutes, resulting in the development of a blue color. The addition of Stop Solution stops the reaction and converts the color to yellow. The intensity of the yellow color is directly proportional to the concentration of hGH in the sample. As shown in FIG. 1, the reverse micelle compositions promoted the absorption of hGH, whereas little to no absorption was detected with control compositions.

7. EXAMPLE

Luteinizing Hormone Releasing Hormone Agonist Reverse Micelles

This example demonstrates that a higher percentage of bioavailability of luteinizing hormone releasing hormone (LHRH) is achieved when LHRH is administered intraduodenally in a reverse micelle formulation than when LHRH is administered intraduodenally in a water-in-oil emulsion formulation.
Preparation of Reverse Micelles
LHRH is a peptide hormone secreted by the hypothalamus (see, e.g., U.S. Pat. No. 4,234,571) with the following amino acid sequence:
p-Glu-His-Trp-Ser-Tyr-Gly-Leu-Arg-Pro-Gly-NH$_2$
(MW=1182 daltons; SEQ ID NO: 1)
LHRH was obtained by synthesis (Polypeptide Labs) as the acetate salt. LHRH was dissolved in acetate buffer (pH 5.1) and prepared in a variety of vehicles as follows.
  a. RM-A12. 1.5 grams of a solution of LHRH was added directly to 8.5 grams of Acconon CC-12 and mixed with vortexing until a transparent dispersion was obtained.
  b. RM-C. Capmul MCM was mixed in a 7:2 ratio with cremophor. To 9 grams of the surfactant mixture, 1 gram of a solution of LHRH was added and mixed with vortexing until the dispersion was transparent.
  c. RM-L: 1.5 grams of a solution of LHRH was added to 8.5 grams of Labrasol and mixed well until a clear dispersion was obtained.
  d. RM-A8: 1.5 grams of a solution of LHRH was added directly to 8.5 grams of Acconon MC-8 and mixed with vortexing until a transparent dispersion was obtained.
  e. RM-A6: 1.5 grams of a solution of LHRH was added directly to 8.5 grams of Acconon CC-6 and mixed with vortexing until a transparent dispersion was obtained.
  f. RM-S: 1.5 grams of a solution of LHRH was added directly to 8.5 grams of Softigen 767 and mixed with vortexing until a transparent dispersion was obtained.
A water-in-oil microemulsion was prepared
  g. W/O ME: 1 gram of a solution of LHRH was added to a mixture of 6 grams of Captex 355, 2 grams of Capmul MCM, and 1 gram of polyoxyethylated(20) sorbitan oleate (Tween 80) and mixed until a transparent microemulsion was obtained. The final composition of the microemulsion is 60% Captex, 20% Capmul MCM, 10% Tween-80, and 10% acetate buffer incorporating LHRH.
Pharmacokinetics of LHRH in Rats
Sprague-Dawley rats (approximately weighing 120 grams each) were catheterized surgically with jugular and duodenal catheters. Each group of rats, 3-5 animals per group, were given 0.4-2.4 mg/kg of LHRH either as free in solution or incorporated in micelles. As further control, several groups of animals were given a solution of free LHRH subcutaneously at a dose of 0.4 mg/kg of body weight. Blood samples were collected at 0, 20, 40, 60, 90, 120, and 240 minutes following administration of LHRH or controls. The time 0 blood collection was obtained approximately 15 minutes before administration of LHRH formulations. Plasma samples were analyzed by a competitive ELISA assay as follows. Plastic 96 well plates were coated with anti-rabbit immunoglobulins followed by addition of rabbit anti-LHRH and biotinylated-LHRH with sample dilutions. Binding of biotinylated LHRH was assayed by development with BRP-avidin and color development with TMB (tetra-methyl-benzidine). Pharmacokinetic parameters were calculated from the data using WinNonLin software (Pharsight). No absorption of intraduodenally administered LHRH was evident in any animal unless formulated in a reverse micellar composition (Table 2, FIG. 2). On the other hand reverse micelles of LHRH in Acconon or Softigen type surfactants administered intraduodenally promoted approximately 10% bioavailability relative to subcutaneous injections of aqueous solution of LHRH. The percent absolute bioavailability obtained from Capmul MCM and Labrasol reverse micelles was about 5% (Table 2).

TABLE 2

Pharmacokinetic Parameters of LHRH in Rats.

| Formulation | Dose (mg/kg) | $C_{max}$ (ng/ml) | AUCinf (min * ng/ml) | % Absolute Bioavailability |
|---|---|---|---|---|
| LHRH solution SC | 0.4 (n = 5) | 79 ± 51.2 | 1888.2 ± 320 | 100% |
| W/O ME ID | 6.0 (n = 3) | 13.4 ± 3.5 | 847.1 ± 61.2 | 3.3 ± 0.2% |
| RM-A12* ID | 4.8 (n = 5) | 13.1 ± 4.8 | 1205.1 ± 307.1 | 5.7 ± 1.4% |
| | 2.4* (n = 5) | 12.2 ± 3.9 | 1009.8 ± 262.8 | 9.8 ± 2.3% |
| | | 7.5 ± 3.5 | 968.9 ± 276.9 | 9.4 ± 2.3% |
| | | 9.1 ± 4.0 | 932.8 ± 314.5 | 8.8 ± 3.0% |
| | | 7.9 ± 2.5 | 929.6 ± 159.6 | 8.7 ± 1.7% |
| RM-A8 ID | 2.4 (n = 5) | 8.9 ± 4.8 | 1217.9 ± 525.9 | 11.8 ± 5.1% |
| RM-A6 ID | 2.4 (n = 5) | 8.4 ± 3.8 | 891.4 ± 68.9 | 8.6 ± 0.6% |
| RM-S ID | 2.4 (n = 5) | 9.9 ± 2.4 | 1132.8 ± 153..2 | 11.1 ± 1.6% |
| RM-C ID | 2.4 (n = 5) | 5.9 ± 1.4 | 541.6 ± 219.8 | 5.2 ± 1.9% |
| RM-L ID | 2.4 (n = 5) | 4.5 ± 0.9 | 377.3 ± 190.6 | 3.7 ± 1.9% |

ID = intraduodenal administration;
SC = subcutaneous administration;
AUCinf = Area Under Curve from time 0 to Infinity;
n = number of rats.
*PK data with RM-A12 was reproduced via four independent experiments.

8. EXAMPLE

Leuprolide Reverse Micelles

This example demonstrates that a higher absolute bioavailability of leuprolide is achieved when leuprolide is administered intraduodenally in a reverse micelle formulation than when leuprolide is administered intraduodenally as a solution formulation in acetate buffer.

Preparation of Softigen Containing Reverse Micelles (RM-S)

Leuprolide is a LHRH agonist which suppresses endogenous gonanotropins, causing a hypogonadal condition with the following amino acid structure: p-Glu-His-Trp-Ser-Tyr-D-Leu-Leu-Arg-Pro-$NHC_2H_5$ (MW=1209 daltons; SEQ ID NO:2). Leuprolide (acetate salt, Polypeptide Labs) was dissolved in an appropriate buffer (for example, 0.1 M sodium acetate) at an appropriate pH (for example, pH=6.0). 1.5 grams of the leuprolide solution was added to 8.5 grams of Softigen 767 and vortex mixed until the dispersion was clear and transparent.

Preparation of Labrasol Containing Reverse Micelles (RM-L)

Leuprolide was dissolved in an appropriate buffer (for example, 0.1 M sodium acetate) at an appropriate pH (for example, pH=6.0). 1.5 grams of the leuprolide solution was added to 8.5 grams of Labrasol and vortex mixed until the dispersion was clear and transparent.

Quantitation of Leuprolide in Reverse Micelle Formulations by HPLC

Leuprolide concentration in reverse micelle (R1 formulations was measured by reversed phase HPLC using a Hewlett Packard 1050 system equipped with a Waters C-18 4.6×250 mm 5 μm column, a Supelguard Discovery C-18 2×4.0 mm guard column and UV Diode array detection at 220 mm. Mobile phase A was 0.1% (v/v) trifluoroacetic acid (TFA) in deionized water and mobile phase B was 0.1% (v/v) TFA in HPLC grade acetonitrile. The run condition was 10-40% B gradient in 25 minutes at a flow rate of 1.5 ml/min. The column was reconditioned with an isocratic hold of 10% B at 0.5 ml/min for 5 minutes and at 1.5 ml/min for additional 10 to 15 minutes. The retention time of leuprolide in this system was between 9 and 14 minutes. The concentration was calculated by using area under curve of the sample peak against a standard curve of 0.01 to 0.8 mg/ml leuprolide acetate versus corresponding area under the curve.

Pharmacokinetics of Leuprolide in Rats

Sprague-Dawley rats (approximately weighing 120 grams each) were catheterized surgically with jugular and duodenal catheters. Each group of rats, 4-5 animals per group, were given 0.4-3.6 mg/kg of leuprolide either as free in solution or incorporated in micelles. As further control, several groups of animals were given a solution of free leuprolide subcutaneously. Blood samples were collected at 0, 20, 40, 60, 90, 120, and 240 minutes following administration of leuprolide or controls. The time 0 blood collection was obtained approximately 15 minutes before administration of leuprolide formulations. The amount of leuprolide released into rat serum or leuprolide in formulation was determined by using competitive enzyme-linked immunosorbent assay (ELISA) (Peninsula Laboratories, Inc). The assay system utilizes goat anti-rabbit IgG for solid phase (microwells) immobilization. The test serum or formulation sample was allowed to react simultaneously with the coated antibody, rabbit anti-leuprolide and biotinylated leuprolide. The biotinylated leuprolide competes for the antibody binding sites with standard or the unknown sample leuprolide. After a two-hour (or overnight) incubation at room temperature, unbound biotinylated peptide was removed by washing, and streptavidin-conjugated horseradish peroxidase (SA-HRP) was added and allowed to bind the immobilized rabbit anti-leuprolide/biotinylated leuprolide complex. After washing away excess SA-HRP, 3,3',5,5'-Tetramethylbenzidine (TMB) was added and incubated for 15 minutes, resulting in the development of a blue color. The addition of Stop Solution stops the reaction and converts the color to yellow. The intensity of the yellow color depends on the quantity of biotinylated leuprolide bound to the immobilized antibody: When more sample leuprolide competes for the limited antibody, less biotinylated leuprolide/SA-HRP can be immobilized, and less color is produced by the substrate.

TABLE 3

Pharmacokinetic parameters of Leuprolide in Rats (mean ± SD).

| Formulation* | Dose (mg/kg) | $C_{max}$ (ng/ml) | $AUC_{inf}$ (min * ng/ml) | % Absolute Bioavailability |
|---|---|---|---|---|
| Leuprolide solution SC | 0.4 (n = 5) | 453 ± 94 | 23845 ± 1579 | 100 |
| Leuprolide solution ID | 2.4 (n = 5) | 6.3 ± 5.3 | 326.0 ± 164.5 | 0.23 ± 0.12 |
| RM-S | 0.4 (n = 4) | 120.6 ± 57.6 | 7864.7 ± 2285.6 | 33.0 ± 9.6 |
|  | 0.4 (n = 5) | 89.5 ± 26.3 | 6130.0 ± 1622.5 | 25.7 ± 6.8 |
|  | 0.4 (n = 5) | 100.0 ± 24.1 | 9456.5 ± 3949.2 | 33.5 ± 7.3 |
|  | 1.2 (n = 4) | 262 ± 61 | 27954 ± 6058 | 39.1 ± 8.5 |
|  | 2.4 (n = 4) | 381 ± 13 | 40371 ± 4926 | 28.2 ± 3.4 |
|  | 2.4 (n = 5) | 404.8 ± 72.9 | 38893.8 ± 7422.8 | 27.2 ± 5.2 |
|  | 3.6 (n = 4) | 520.6 ± 162.9 | 47498.4 ± 18365 | 22.1 ± 8.6 |
| RM-L ID | 0.4 (n = 3) | 106.2 ± 10.4 | 4696.2 ± 304.4 | 19.7 ± 1.3 |

*RM-S = Softigen 767 reverse micelle
*RM-L = Labrasol reverse micelle
ID = intraduodenal administration;
AUCinf = Area Under Curve from time 0 to Infinity;
SC = subcutaneous;
n = number of rats As can be seen from the data in Table 3, the intraduodenal bioavailability of leuprolide from a solution formulation (0.1 M acetate pH 6.0) is very low (about 0.2%) whereas the intraduodenal bioavailability from the RM-S is about 22% to about 39%. Essentially the same bioavailability was obtained in a repeated study with RM-S using 2.4 mg/kg dose of leuprolide, emphasizing the consistency and reproducibility in the absorption data. The bioavailability of leuprolide was dose dependent. That is to say that the higher the dose the higher the Cmax and AUC and the lower the percent absolute bioavailability (Table 3).

Pharmacokinetics of Leuprolide in Dogs

Beagle dogs (3 female and 3 male weighing 8-10 kg each) were catheterized surgically with duodenal catheters. For each treatment, the dogs were given 0.4-2.4 mg/kg of leuprolide either in solution or incorporated in micelles. The treatments were administered via the duodenal catheter. For the positive control, the dogs were given a solution of free leuprolide by subcutaneous injection. Blood samples were collected from cephalic catheters or the jugular vein at 0, 15, 30, 45, 60, 90, 120, 240, 360, 480, and 1440 minutes following administration of leuprolide or controls. Leuprolide concentration levels are illustrated in the standard curves in FIG. 4. The time 0 blood collection was obtained approximately 10 minutes before administration of leuprolide formulations. The amount of leuprolide released into dog serum was determined by using a competitive enzyme-linked immunosorbent assay (ELISA) from Peninsula Laboratories, Inc. which utilizes goat anti-rabbit IgG for solid phase (microwell) immobilization. The test serum was allowed to react simultaneously with the coated antibody, rabbit anti-leuprolide and biotinylated leuprolide. After two-hour incubation at room temperature, unbound biotinylated peptide was removed by washing, and streptavidin-conjugated horseradish peroxidase (SA-HRP) was added and allowed to bind the immobilized rabbit anti-leuprolide/biotinylated leuprolide complex. After washing away excess SA-HRP, 3,3'5,5'-Tetramethylbenzidine dihydrochloride (B) was added and incubated for 15 minutes, resulting in the development of a blue color. The addition of stop solution stops the reaction and converts the color to yellow. Leuprolide in the samples was quantified by non-linear regression analysis of the standard curve and sample optical density values. Pharmacokinetic parameters are calculated using a pharmacokinetic software with a non-compartmental model.

TABLE 4

Pharmacokinetic parameters of Leuprolide in Dogs (mean ± SD)

| Formulation* | Dose** (mg/kg) | $C_{max}$ (ng/ml) | $AUC_{inf}$ (min * ng/ml) | % Absolute Bioavailability |
|---|---|---|---|---|
| Leuprolide solution SC | 0.4 (n = 6) | 412.4 ± 163.3 | 54282 ± 10354 | 100 |
| RM-S ID | 0.4 (n = 6) | 133.8 ± 38.4 | 16348 ± 5572 | 30.1 ± 10.3 |
|  | 2.4 (n = 6) | 621.9 ± 74.2 | 71431 ± 21910 | 21.9 ± 6.7 |
| RM-L ID | 2.4 (n = 6) | 542.9 ± 172.7 | 59247 ± 27248 | 18.2 ± 8.4 |

*RM-S = Softigen 767 reverse micelle
*RM-L = Labrasol reverse micelle
**Doses of excipients were at least 13 times less than those used in the rat studies in Table 3
ID = intraduodenal administration;
AUCinf = Area Under Curve from time 0 to Infinity;
SC = subcutaneous;
n = number of rats

9. EXAMPLE

Reverse Micelle Capsules

Preparation of Reverse Micelle Capsules

Reverse micelles that are compatible with gelatin capsules were prepared by mixing an excipient, for example, Softigen 767 or Labrasol, with a leuprolide solution in buffer at an appropriate ratio, for example, 85:15 w/w. Based on the weight of the animals, an appropriate amount of reverse micelle containing leuprolide was placed into the body part of a capsule of suitable size (for example, size 00 or 13 gelatin capsules) and the cap was then put in place and locked. The capsule was sealed by applying a few microliters of an alcoholic solution (for example, 1:1 isopropanol-water solution) and allowing the solution to dry.

Enteric Coating of Reverse Micelle Capsules

Enteric coating of a reverse micelle capsule was performed using techniques known to others in the art. (Enteric Coating of Hard Gelatine Capsules Application of EUDRAGIT® L 30 D-55, Rohm Pharma Polymers Application Note 4.1.9.4) A modified coating method and a modified coating solution were also used. Specifically, Eudragit L30D-55 (10.56 g) was diluted with 7.9 g of distilled water and mixed with 0.63 g of triethyl citrate. To this, 0.134 g of 30% Tween 80 was added. The resulting suspension was stirred for 30 minutes. The coating solution was either used as is, or the pH of the coating solution was adjusted to a desired level (for example, pH 5.5) so that the coated capsule would have a better dissolution profile in the duodenum. A dipping method was used for the coating of the capsules. The capsules (especially the size 13 capsules) were held by a multi-port valve-controlled vacuum suction device, which was developed by the same authors, during the coating processes. Alternatively, the capsules were coated using a coater.

Dissolution Test Using a Continued In Situ Monitoring System

Dissolution of the capsules was tested using a USP test method on a dissolution test station (VanKel VK 7000). (USP Physical Tests <711> Dissolution and <724> Drug Release) Automation of the sampling and measurement was achieved by using a continued in situ monitoring system developed by the applicants. Specifically, a HPLC solvent inlet filter was attached to the inlet of a sample intake tube inserted into the dissolution test vessel. The intake tube was connected to a HPLC pump which was directly connected to one or more detectors such as diol array detectors, RI detectors, fluorescent detectors, UV detectors, and so forth, and combinations of such, in a HPLC system. The out-flow from the detector was directed back into the test vessel by another tube. Signals from the detectors such as UV absorption at multiple wavelengths of choice and UV spectra of the sample were continuously collected and stored by the HPLC system and data was analyzed using the HPLC software. Plots of the signals against time, termed here as "Dissolugrams", represent the dissolution profiles of the coating material, the capsule (220 nm) and the release of the reverse micelle (220 and 540 nm) and Leuprolide (280 nm). The enteric coated reverse micelle capsules were stable in the acid stage for at least 2 hours as indicated in the dissolugrams by the relatively unchanged UV 220, 280 and 540 nm signals. In buffer stage, the enteric coated capsules dissolved within 10 minutes according to the dissolugrams. The non-coated reverse micelle capsules dissolved within 3 minutes in the acid stage according to the dissolugrams.

Model compounds with special UV absorption wavelengths such as dimethylaminopyridine (280 nm), Bacto Methylene Blue (340 nm) or fluorescent compounds were also used replacing leuprolide in the reverse micelle in capsules for the dissolution tests.

10. EXAMPLE

Demonstration of the Formation of Reverse Micelles Using Different Molecular Size Amorphous Dextran Several fluorescent labeled dextrans of varying molecular weights were used to form reverse micelles. Either FITC-Dextran 4,000 daltons, 10,000 daltons, or 20,000 daltons were dissolved in water at different ratios of water to surfactant. Stable reverse micelles were formed at up to 50% total water phase as determined by the quenching of FITC fluorescence and obtained a transparent dispersion. Fluorescence of FITC could be retrieved by dilution of the stable reverse micelles into excess water, indicating extrusion of the water-soluble dextran from the surfactant phase.

11. EXAMPLE

Demonstration of the Formation of Reverse Micelles by Electrical Resistance Measurements Reverse micelles (RMs) where the internal or dispersed phase is aqueous are expected to exhibit low electrical conductance or high resistance. Thus, conductivity or resistivity measurements can be used to confirm the reverse micellar structure.

To demonstrate this point the following experiment was conducted: Various RMs were prepared by mixing 15% (w/w) 1× phosphate-buffered saline (PBS) with 85% (w/w) corresponding excipients. Subsequently, deionized water was added incrementally to up to 90% total content of water by weight. The resistivity of solution was measured incrementally using Millicell-ERS electrode system (Millipore). The resistivity of deionized water was exceed measurable range of electrode (>19.99 KOhms), of tested excipients (0% water) were about 15.5 KOhms and of 1×PBS was 2-3 Ohms. RM containing 15% PBS still showed high resistance due to the fact that the most of electrolytes are remained in core of reverse micellar structure within the continuous phase of excipients. RM systems using different surfactants exhibited similar pattern in the drop of resistivity as increasing % water. Sharp drop in resistivity indicated release of encapsulated electrolytes from the core of the RM system into medium upon dilution with non-conductive deionized water. The resistivity reached plateau (at about 15 Ohms) after exceeding 40% total water content in the system. This implies that the reverse micelle system (L2 phase) has been converted into regular micelle (L1 phase) after this point where the continuous phase is aqueous (water).

12. EXAMPLE

Demonstration of the Oral Bioavailability of Rhodamine Dextran in Reverse Micelle Two rhodamine dextran containing reverse micelles were prepared separately by vortex mixing Softigen 767 (8.5 g) and a rhodamine dextran solution (1.5 ml, Mw.=3,000 Da). Sprague-Dawley rats (approximately weighing 120 grams each) were catheterized surgically with jugular and duodenal catheters. Groups of 5 rats were given separately 1.2 mg/kg of a rhodamine dextran (Mw. 3,000 Da) in reverse micelles through the duodenal catheter, or 0.4 mg/kg of a rhodamine dextran (Mw. 3,000 Da) in solution subcutaneously. Blood samples were collected at 0, 20, 40, 60, 90, 120, and 240 minutes following the administration of the test articles. The time 0 blood collection was obtained approximately 15 minutes before administration of the test articles. The amount of rhodamine dextran was determined by measuring the fluorescent intensity of the samples on fluorescent plate reader. Percent bioavailability was calculated from AUC of the rhodamine dextran plasma level in the groups received reverse micelle formulations against the AUC of the corresponding rhodamine dextran plasma level in the groups received control solutions. The bioavailability of the rhodamine dextran (Mw. 3,000 Da) was thus determined to be 18%. (Table 5)

TABLE 5

Pharmacokinetic Parameters of Rhodamine Dextran (Mw 3000 Da) in Rats (mean ± SD)

| Formulation* | Dose (mg/kg) | $C_{max}$ (ng/ml) | $AUC_{inf}$ (min * ng/ml) | % Absolute Bioavailability |
|---|---|---|---|---|
| Rhodamine dextran solution | 0.4 (n = 3) | 258.5 ± 39.6 | 15769 ± 2840 | 100 |
| Rhodamine dextran RM-S | 1.2 (n = 3) | 220.1 ± 81.6 | 8485 ± 5293 | 17.9 ± 11.2 |

13. EXAMPLE

Stabilized Reverse Micelles with Different Polymers

PLGA Microparticles in Acconon/Aqueous LHRH Reverse Micelle

PLGA microparticles (18 mg, RG504) were suspended in dichloromethane (0.2 ml). The resultant suspension was added slowly, with rapid stirring, to 0.5 ml of a reverse micelle consist of Acconon CC-6 or Acconon CC-12 (85% w/w) and LHRH aqueous solution (15%, w/w). The dichloromethane was then removed at reduced pressure to give a suspension.

PLGA Microparticles in Acconon/Carbopol/Aqueous LHRH Reverse Micelle

Carbopol 980NF (16 mg) was suspended in Acconon CC-6 or Acconon CC-12 (9.8 g) then mixed with a LHRH solution (1.7 ml). To 1 ml of this reverse micelle was added slowly, with rapid stirring, a PLGA (20 mg, RG504) suspension in dichloromethane (0.2 ml). Dichloromethane was then removed at reduced pressure to yield a suspension.

Leuprolide Reverse Micelles Stabilized with Carbapol/Carrageenan

Softigen 767 (5.1 g) was mixed with Carbopol 980NF (90 mg). To this was added 1.0 ml of a leuprolide in 0.1 M sodium acetate solution, pH=6.0 and vortex mixed. After a few hours, 100 microliters of a Carrageenan solution was added and the mixture was vortex mixed to form a gel.

14. EXAMPLE

Stabilized Reverse Micelles with Hydrophobic Molecules

Leuprolide Reverse Micelles Stabilized with Eudragit RSPO/Carbopol

Leuprolide reverse micelles containing Softigen 767 (5.1 g) and a leuprolide in 0.1 M sodium acetate solution (0.9 ml, pH=6.0) were mixed by a mixer with Eudragit RSPO (600 mg). After 3 hours, the mixture was further mixed with Carbopol 980NF (90 mg) to form a suspension.

These examples demonstrate various methods of stabilization of reverse micelles with polymeric stabilizers.

N.F. White Beewax (8.9 mg) was pre-heated to 65° C. in a vial with rapid stirring. The wax was mixed with 1 ml of reverse micelle containing Acconon CC-6 or Acconon CC-12 (85% w/w) and an aqueous LHRH solution (15% w/w) to yield a clear reverse micelle. The mixture was then cooled slowly to room temperature to give the resulting suspension.

N.F. White Beewax (49 mg) was pre-heated to 65° C. in a vial with rapid stirring. The wax was mixed with 1 ml of reverse micelle containing Acconon CC-6 or Acconon CC-12 (85% w/w) and an aqueous LHRH solution (15% w/w) to yield a clear reverse micelle. The mixture was then cooled slowly to room temperature to give a semi-solid suspension.

Using a gelling agent: Carbopol 980NF (16 mg) was suspended in Softigen 767 (9.8 g), then mixed with a leuprolide solution (1.7 mL). The clear suspension was then mixed with 6.5 mg of Carbopol 980NF to form a thick gel.

15. EXAMPLE

Interfacial Polymerization of Reverse Micelles Containing LHRH and Leuprolide These examples demonstrate the method of polymerization of reverse micelles of the present invention.

Polyethylcyanoacrylate Stabilized LHRH Reverse Micelles

Reverse micelle (1 g) consist of Acconon CC-6 or Acconon CC-12 (85% w/w) and aqueous LHRH solution (15% w/w) was mixed with, under rapid stirring, 200 microliters of an ethylcyanoacrylate solution (100 mg/ml) in dichloromethane. The mixture was stirred at room temperature for 2 hours then the dichloromethane was removed under reduced pressure to give a reverse micelle.

Polyethylcyanoacrylate Stabilized Leuprolide Reverse Micelles (1)

Revere micelle (1 g) consist of Capmul MCM (85% w/w) and a leuprolide solution (15% w/w, in 0.1 M sodium acetate buffer, pH 6.0) was mixed with, under rapid stirring, 200 microliters of an ethylcyanoacrylate solution (100 mg/mL) in dichloromethane. The mixture was stirred at room temperature for 2 hours then the dichloromethane was removed under reduced pressure to give a reverse micelle.

Polyethylcyanoacrylate Stabilized Leuprolide Reverse Micelles (2)

Polyethylcyanoacrylate containing Capmul MCM reverse micelle (1 g, from (1)) was mixed with another reverse micelle consisting of Softigen 767 (85% w/w) and a leuprolide solution (15% w/w, in 0.1 M sodium acetate buffer, pH 6.0).

Polyethylcyanoacrylate Stabilized Leuprolide Reverse Micelles (3)

Leuprolide reverse micelle (6 g) containing Softigen 767 (5.1 g) and a leuprolide in 0.1 M sodium acetate solution (0.9 ml, pH=6.0) was vortex mixed with an ethylcyanoacrylate (360 mg) in dichloromethane solution. After 2 hours, the solvent was removed at reduced pressure. To this was added another 3 g of the above mentioned leuprolide reverse micelle and the mixture was vortex mixed.

Leuprolide Reverse Micelles Stabilized by Polymerization of Polymerizable Fatty Acid Derivatives 2,4-Octadecadienoic acid poly(ethylene glycol) ester (2,4-ODPEG, U.S. Pat. No. 6,187,335, 0.475 g) and Softigen 767 (4.625 g) was vortex mixed with 1.0 ml of a leuprolide in 0.1 M sodium acetate solution, pH=6.0. To this was added, with rapid vortex, 100 microliters of a dimethylphenylacetophenone (DMPA) in dichloromethane solution (0.18 g/ml). The polymerization was carried out by exposing the reverse micelle to a UV 365 nm light source to a desired level (for example, 18%). Aliquots of the reverse micelle were taken at different time points and diluted with distilled water. The polymerization level was monitored by measuring the absorbance of diluted samples at 254 nm.

LHRH Reverse Micelles Stabilized by Polymerization of Polymerizable Fatty Acid Derivatives A stable LHRH micellar drug delivery system was made as follows: Acconon CC-12 (0.5 g) was mixed with (2,4-octadecadienoyl) poly(ethylene glycol) succinate (OPS, 0.05 g). An aqueous LHRH solution (15% w/w) was then added to the mixture under rapid stirring and mixed with vortexing until a transparent dispersion was obtained. To create a polymer of OPS at the interface, DMPA was added (dimethoxyphenylacetylphenone, 5% mol/mol of 2, 4 OPS) and the resulting clear solution was irradiated with a 365 nm UV lamp at 4 mw/cm$^2$ for 1 hour. Polymerization progress was monitored by measuring the disappearance of the absorption at 254 nm. Because of the free hydrophilic groups, OPS primarily interacted at the water interface with the fatty acid tail dissolved in the hydrophobic moiety of the surfactant. The polymerization level reached approximately 70% as measured by the reduction of characteristic diene absorption at 254 nm. Polymerization of OPS in the surfactant mixture and exposure to ultraviolet light at 365 nm did not harm the peptide LHRH contained in the central water core. The polymerized micelle formulation was exposed to either simulated gastric fluid or water and the presence of LHRH in the external water milieu is measured over time using the ELISA method described above. Compared with the non-polymerized micelle formulation, LHRH leaks out of the central water core much slower in the polymerized micelle.

16. EXAMPLE

Quantitation of Leuprolide and LHRH in Stabilized Reverse Micelles

Samples of stabilized reverse micelles containing leuprolide or LHRH were processed according to the polymer contents in the reverse micelles to release leuprolide or LHRH and to remove most of the polymers. Specifically, for polyalkylcyanoacrylates, polyacrylates or polyacrylic acids containing stabilized reverse micelles, samples were first dissolved in an appropriate amount of acetonitrile, mixed with methanol or water then filtered. The filtrates were then analyzed by the HPLC methods for Leuprolide or LHRH specified in the earlier examples. For polymerizable fatty acid derivatives containing reverse micelles, samples were diluted with acetonitrile and used directly for HPLC analysis. For reverse micelles containing polymers insoluble in methanol-water mixtures, samples were extracted with a methanol-water mixture and filtered. The filtrate was used for HPLC analysis. For reverse micelles containing hydrophobic stabilizers, samples were extracted with a methanol-water mixture and filtered. The filtrate was used for HPLC analysis.

17. EXAMPLE

Bioavailability of LHRH or Leuprolide Using Stabilized Reverse Micelles

Bioavailability of LHRH Using Stabilized Micelles.

Stabilized LHRH Acconon-CC-12/OPS reverse micelles are given to Sprague-Dawley rats (~120 gms) surgically catheterized with jugular and duodenal catheters. Each group of rats, 3 animals per group, are given 600 micrograms of LHRH either as free in solution or complexed in micelles or polymerized micelles. Blood samples are collected at 0, 20, 40, 60, 90, 120, 240, 360, and 480 minutes following administration of LHRH or controls. The time 0 blood collection is obtained approximately 15 minutes before administration of LHRH formulations. Plasma samples are analyzed by a competitive ELISA assay as follows. Plastic 96 well plates are coated with anti-rabbit immunoglobulins followed by addition of rabbit anti-LHRH and biotinylated-LHRH with sample dilutions. Binding of biotinylated LHRH is assayed by development with HRP-avidin and color development with TMB (tetra-methyl-benzidine). Pharmacokinetic parameters are calculated from the data using WinNonLin software (Pharsight).

Bioavailability of Leuprolide Using Stabilized Micelles.

Sprague-Dawley rats (approximately weighing 120 grams each) are catheterized surgically with jugular and duodenal catheters. Each group of rats, 4-5 animals per group, are given 0.4-3.6 mg/kg of leuprolide either as free in solution or incorporated in stabilized micelles. As further control, several groups of animals are given a solution of free leuprolide subcutaneously. Blood samples are collected at 0, 20, 40, 60, 90, 120, 240, 360, and 480 minutes following administration of leuprolide or controls. The time 0 blood collection is obtained approximately 15 minutes before administration of leuprolide formulations. The amount of leuprolide released into rat serum or leuprolide in formulation is determined by using competitive enzyme-linked immunosorbent assay (ELISA) (Peninsula Laboratories, Inc). The assay system utilizes goat anti-rabbit IgG for solid phase (microwells) immobilization. The test serum or formulation sample is allowed to react simultaneously with the coated antibody, rabbit anti-leuprolide and biotinylated leuprolide. The biotinylated leuprolide competes for the antibody binding sites with standard or the unknown sample leuprolide. After a two-hour (or overnight) incubation at room temperature, unbound biotinylated peptide is removed by washing, and streptavidin-conjugated horseradish peroxidase (SA-HRP) is added and allowed to bind the immobilized rabbit anti-leuprolide/biotinylated leuprolide complex. After washing away excess SA-HRP, 3,3',5,5'-Tetramethylbenzidine (TMB) is added and incubated for 15 minutes, resulting in the development of a blue color. The addition of Stop Solution stops the reaction and converts the color to yellow. The intensity of the yellow color depends on the quantity of biotinylated leuprolide bound to the immobilized antibody. When more sample leuprolide competes for the limited antibody, less biotinylated leuprolide/SA-HRP can be immobilized, and less color is produced by the substrate.

18. EXAMPLE

Release Profile in Simulated Intestinal Fluid

This example demonstrates the use of reverse micelles of the present invention for delivery of biologically active molecules.

The release profile of various reverse micelles are investigated by mixing the reverse micelle with simulated intestinal fluid at a ratio of 1:5. The samples are, at different time points, either used directly for HPLC analysis or filtered through a 0.2 micrometer filter then analyzed by HPLC. HPLC analysis is performed using a size exclusion column (TSK-GEL 3000SW, 10 micrometers) on a HP 1090 HPLC system equipped with a DAD detector. Mobile phase: PBS (1×); flow rate: 1 ml/min isocratic.

The present invention is not to be limited in scope by the exemplified embodiments, which are intended as illustrations of single aspects of the invention. Indeed, various modifications of the invention in addition to those shown and described herein will become apparent to those skilled in the art from the foregoing description. Such modifications are intended to fall within the scope of the appended claims.

All patents, patent applications and non-patent publications cited herein are incorporated by reference in their entirety to the same extent as if each individual patent, patent application or non-patent publication was specifically and individually indicated to be incorporated herein by reference.

What is claimed is:

1. A reverse micelle composition which promotes absorption of a biologically active molecule by mucosal tissue comprising:
   (a) a surfactant comprising one fatty acid ester, wherein the one fatty acid ester is between 6 and 12 carbon atoms in length, and further wherein the surfactant is a p-glycoprotein inhibitor;
   (b) a hydrophilic phase, wherein the hydrophilic phase is present in an amount from about 0 to about 70% by weight;
   (c) a biologically active molecule, wherein the biologically active molecule comprises at least one leutinizing hormone releasing hormone (LHRH) agonist, an analog thereof or LHRH; and
   (d) a polymerized, water insoluble polymeric stabilizer, wherein the stabilizer is a natural polymer, a synthetic polymer or a mixture thereof.

2. Th reverse micelle composition of claim 1, wherein the fatty acid ester is derivatized with acetic acid, citric acid, lactic acid, succinic acid, tartaric acid or mixtures thereof.

3. The reverse micelle composition of claim 1, wherein the fatty acid ester is a caprylic acid of capric acid.

4. The reverse micelle composition of claim 1, wherein the hydrophilic phase comprises, water, glycerol, sorbitol, mannitol, propylene glycol, ethylene glycol, polyethylene glycol or mixtures thereof.

5. The reverse micelle composition of claim 4, wherein the hydrophilic phase further comprises a buffering agent, a tonicity agent, an oxidizing agent, a reducing agent, an antimicrobial agent, a preservative, a stabilizing agent, or a mixture thereof.

6. The reverse micelle composition of claim 1, wherein the hydrophilic phase is present in an amount from about 0 to about 50% by weight.

7. The reverse micelle composition of claim 6, wherein the hydrophilic phase is present in an amount from about 5 to 25% by weight.

8. The reverse micelle composition of claim 1, wherein the fatty acid ester has an hydrophile-lipophile balance (HLB) of about 1 to about 20.

9. The reverse micelle composition of claim 8, where the fatty acid ester has an HLB of about 5 to about 15.

10. The reverse micelle composition of claim 1, wherein the LHRH agonist is leuprolide, goserelin, nafarelin or histrelin.

11. The reverse micelle composition of claim 1, wherein the concentration of the biologically active molecule is more than 0.1 mg/ml soluble in the hydrophilic phase.

12. The reverse micelle composition of claim 11, wherein the concentration of the biologically active molecule is more than 1 mg/ml soluble in the hydrophilic phase.

13. The reverse micelle composition of claim 1, wherein the concentration of the biologically active molecule is from 0.05 to 100 mg/ml.

14. The reverse micelle composition of claim 1, wherein the polymer is formed from a polymerizable fatty acid monomer.

15. The reverse micelle composition of claim 1, wherein the polymer is formed by interfacial ionic polymerization with water or other initiators.

16. The reverse micelle composition of claim 1, wherein the polymer is formed by condensation of cyanoacrylates, including alkylcyanoacrylates.

17. The reverse micelle composition of claim 1, wherein the polymer is formed from condensation of ethyl 2-cyanoacrylate.

18. The reverse micelle composition of claim 1, wherein the synthetic polymer is polylactide, polyglycolide, a mixture of polylactide and polyglycolide, polycaprolactone, polyortho esters, polyalkylenes, polyacrylamides, poly(hydroxy acids), polyanhydrides, polyorthoesters, polyacalate, polyvinyl alcohols, blends or copolymers thereof.

* * * * *

UNITED STATES PATENT AND TRADEMARK OFFICE
CERTIFICATE OF CORRECTION

PATENT NO. : 8,535,650 B2
APPLICATION NO. : 10/497775
DATED : September 17, 2013
INVENTOR(S) : Constantinides et al.

Page 1 of 2

It is certified that error appears in the above-identified patent and that said Letters Patent is hereby corrected as shown below:

In the Specification:

Col. 3, line 54: between the word "are" and the word "contact" insert the word --in--;

Col. 4, line 49: the word "endromettiosis" should read "endrometriosis";

Col. 4, line 55: the word "lelomyomata" should read "leiomyomata";

Col. 4, line 61: the word "catamental" should read "catamenial";

Col. 6, line 18: the word "compromise" should read "compromising";

Col. 9, line 11: between the word "to" and the word "animal" insert the word --an--;

Col. 9, line 18: the word "lelomyomata" should read "leiomyomata";

Col. 9, line 19: the word "endometiral" should read "endometrial";

Col. 9, line 24: the word "anaemia" should read "anemia";

Col. 9, line 24: the word "catamental" should read "catamenial";

Col. 9, line 25: delete the "." before the ",";

Col. 10, line 12: between the word "diagnosis" and the word "said" insert the word --of--;

Col. 10, line 18: between the word "methods" and the word "diagnosing" insert the word --for--;

Col. 10, line 20: between the word "administering" and the word "an" insert the word --to--;

Col. 10, line 25: after the word "methods" insert the word --for--;

Col. 12, line 9: insert --"-- before the word "Mucosal";

Col. 12, line 11: delete the word "the";

Col. 13, line 3: between the word "may" and the word "combined" insert the word --be--;

Col. 13, line 12: between the word "delivery" and the word "a" insert the word --of--;

Col. 13, line 17: between the word "delivery" and the word "a" insert the word --of--;

Col. 13, line 34: delete the word "aerosol";

Col. 14, line 49: the word "miceule" should read "micelle";

Signed and Sealed this
Fifth Day of November, 2013

Teresa Stanek Rea
*Deputy Director of the United States Patent and Trademark Office*

CERTIFICATE OF CORRECTION (continued)
U.S. Pat. No. 8,535,650 B2

Col. 17, line 50: the word "WV" should read "UV";

Col. 17, line 53: the word "WV" should read "UV";

Col. 18, line 22: the word "mixture" should read "mixtures";

Col. 19, line 21: the word "ebacic" should read "sebacic";

Col. 21, line 12: delete the second occurrence of "neomycin";

Col. 21, line 54: delete the ")" after the word "gamma";

Col. 22, line 36: between the word "may" and the word "further" insert the word --be--;

Col. 23, line 1: insert a --.-- after the word "effect";

Col. 23, line 21: the word "weigh" should read "weight";

Col. 23, line 32: the word "weigh" should read "weight";

Col. 23, line 35: the word "weigh" should read "weight";

Col. 23, line 37: the word "weigh" should read "weight";

Col. 23, line 64: the word "lelomyotama" should read "leiomyomata";

Col. 23, line 65: the word "endometiral" should read "endometrial";

Col. 23, line 67: the word "premensual" should read "premenstrual";

Col. 24, line 3: the word "anaemia" should read "anemia";

Col. 24, line 3: the word "catamental" should read "catamenial";

Col. 24, line 4: delete the "." before the ",";

Col. 24, line 53: the word "vaccines" should read "vaccine";

Col. 33, line 67: the phrase "was exceed" should read "exceeded the";

Col. 34, line 1: insert the word --the-- before the word "electrode";

Col. 34, line 1: delete the word "of";

Col. 34, line 2: delete the word "of";

Col. 34, line 7: the word "pattern" should read "patterns";

Col. 35, line 61: the word "consist" should read "consisting";

Col. 36, line 3: the word "consist" should read "consisting".